(12) United States Patent
Kovacs et al.

(10) Patent No.: US 8,697,034 B2
(45) Date of Patent: Apr. 15, 2014

(54) HYPERPOLARIZED 89-YTTRIUM AND METHODS RELATING THERETO

(75) Inventors: Zoltan Kovacs, Lewisville, TX (US); Matthew E. Merritt, Euless, TX (US); A. Dean Sherry, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1008 days.

(21) Appl. No.: 12/576,743

(22) Filed: Oct. 9, 2009

(65) Prior Publication Data
US 2010/0092396 A1 Apr. 15, 2010

Related U.S. Application Data

(60) Provisional application No. 61/104,487, filed on Oct. 10, 2008.

(51) Int. Cl.
*A61B 5/055* (2006.01)
*G01V 3/00* (2006.01)

(52) U.S. Cl.
USPC .................. 424/9.363; 424/9.36; 324/307

(58) Field of Classification Search
USPC ............... 424/9.3, 9.36, 9.364, 9.365, 9.363; 324/307
See application file for complete search history.

(56) References Cited

U.S. PATENT DOCUMENTS

| | | | |
|---|---|---|---|
| 6,673,333 B1 * | 1/2004 | Meade et al. ................ | 424/9.35 |
| 2006/0173282 A1 | 8/2006 | Ardenkjaer-Larsen et al. ............... | 600/420 |
| 2008/0260649 A1 * | 10/2008 | Thaning et al. .............. | 424/9.36 |
| 2008/0279745 A1 * | 11/2008 | Dorn et al. ................... | 423/263 |
| 2009/0302842 A1 * | 12/2009 | Griffin et al. ................ | 324/309 |

FOREIGN PATENT DOCUMENTS

| | | |
|---|---|---|
| WO | WO 91/12024 | 8/1991 |
| WO | WO 96/39367 | 12/1996 |
| WO | WO 97/09633 | 3/1997 |
| WO | WO 98/39277 | 9/1998 |

OTHER PUBLICATIONS

Merritt, M. et al., JACS, 2007, 129, p. 12942-43, Supporting Information.*
Abragam and Goldman, In: *Nuclear Magnetism: Order and Disorder*, Oxford University Press, Oxford, 1982.
Adam et al., "$^{89}$Y spin-spin relaxation times are not pH dependent," *J. Magn. Reson.*, 33:655, 1979.
Ardenkjaer-Larsen et al., "Increase in signal-to-noise ratio of > 10,000 times in liquid-state NMR," *Proc. Natl. Acad. Sci. USA*, 100:10158-10163, 2003.
Blazina et al., "Application Note: Influence of trityl radical on the DNP process," Oxford Instruments Molecular Biotools Ltd., Tubney Woods, Oxon, UK, 2006.
Brun et al., The nuclear magnetic moments of $K^{41}$, $Y^{87}$, $Ag^{107}$ and $Ag^{109}$, *Phys. Rev.* 93:172-3, 1954.
Comment et al., "Design and performance of DNP prepolarizer coupled to a rodent MRI scanner," *Concepts Magnetic Reson. (B) Magentic Reson. Eng.*, 31B:255-269, 2007.
Day et al., "Detecting tumor response to treatment using hyperpolarized 13C magnetic resonance imaging and spectroscopy," *Nature Med.*, 13:1382-7, 2007.
Esqueda et al., "A new gadolinium-based MRI zinc sensor," *J. Amer. Chem. Soc.*, 131:11387-11391, 2009.
Gerfen et al., "High frequency (140 GHz) dymanic nuclear polzarization: polarization transfer to a solute in frozen aqueous solution, *J. Chem. Physics*, 102:94949, 1995.
Golman and Petersson, "Metabolic imaging and other applications of hyperpolarized 13C1," *Acad. Radiol.*, 13:932-942, 2006.
Golman et al., "Cardiac metabolism measured noninvasively by hyperpolarized 13C MRI," *Magnetic Reson. Med.*, 59:1005-1013, 2008.
Golman et al., "Molecular imaging with endogenous substances," *Proc. Natl. Acad. Sci. USA*, 100:10435-10439, 2003.
Golman et al., "Real-time metabolic imaging," *Proc. Natl. Acad. Sci. USA*, 103:11270-11275, 2006.
Hassler et al., "$^{89}$Yttrium nuclear magnetic resonance studies," *Phys.*, 280:117-123, 1977.
Hindman, "Proton resonance shift of water in the gas and liquid states," *J. Chem. Phys.*, 44:4582, 1966(Abstract only).
Holz and Horrocks, "Yttrium-89 NMR spectroscopy, a new probe for calcium-binding proteins," *J. Magn. Reson.*, 89:627-63, 1990.
Hu et al., "Dynamic nuclear polarization with biradicals," *J. Am. Chem. Soc.*, 126:10844-10845, 2004.
Joo et al., "In situ temperature jump high-frequency dynamic nuclear polarization experiments: enhanced sensitivity in liquid-state NMR spectroscopy," *J. Am. Chem. Soc.*, 128:9428-32, 2006.
Kalman et al., "Potentiometric and relaxometric properties of a gadolinium-based MRI contrast agent for sensing tissue pH," *Inorganic Chem.*, 46:5260-5270, 2007.
Kurhanewicz et al., "Current and potential applications of clinical 13C MR spectroscopy," *J. Nucl. Med.*, 49:341-344, 2008.
Levy et al., "Yttrium-89 NM. A possible spin relaxation probe for studying metal ion interactions with organic ligands," *J. Magnetic Reson.*, 40:167-173, 1980.
Maly et al., "A 140 GHz prepolarizer for dissolution dynamic nuclear polarization," *J. Chem. Physics*, 128:241102, 2008.
Merritt et al., "Dipolar cross-relaxation modulates signal amplitudes in the (1)H NMR spectrum of hyperpolarized [(13)C]formate," *J. Magnetic Reson.*, 189:280-285, 2007.
Merritt et al., "Hyperpolarized (89)Y offers the potential of direct imaging of metal ions in biological systems by magnetic resonance," *J. Amer. Chem. Soc.*, 129:12942-12943, 2007.
Merritt et al., "Hyperpolarized 13C allows a direct measure of flux through a single enzyme-catalyzed step by NMR" *Proc. Natl. Acad. Sci. USA*, 104:19773-19777, 2007.

(Continued)

*Primary Examiner* — Michael G Hartley
*Assistant Examiner* — Leah Schlientz
(74) *Attorney, Agent, or Firm* — Fulbright & Jaworski LLP

(57) ABSTRACT

The present invention relates to the preparation of hyperpolarized $^{89}$Y. Hyperpolarized $^{89}$Y may be used as nuclear magnetic resonance (NMR) and magnetic resonance imaging (MRI) agents for sensitive detection and imaging.

45 Claims, 10 Drawing Sheets

(56) References Cited

OTHER PUBLICATIONS

Overhauser, "Polarization of nuclei in metals," *Physical Review*, 92:411-415, 1953.

Patyal et al., "Longitudinal relaxation and diffusion measurements using magnetic resonance signals from laser-hyperpolarized 129Xe nuclei," *J. Magn. Reson.*, 126:58-65, 1997.

Ren et al., "Imaging the tissue distribution of glucose in livers using a PARACEST sensor," *Magn. Reson. Med.*, 60:1047-55, 2008.

Slade et al., "Application note: Characterising solid-state DNP," Oxford Instruments Molecular Biotools Ltd., Tubney Woods, Oxon, UK, 2006.

Terreno et al., "Enantioselective recognition between chiral alpha-hydroxy-carboxylates and macrocyclic heptadentate lanthanide(III) chelates," *Inorganic Chem.*, 42:4891-4897, 2003.

Wolber et al., "Generating highly polarized nuclear spins in solution using dynamic nuclear polarization," *Nucl. Inst. Meth. Phys. A*, 526:173, 2004.

Woods et al., "Synthesis, relaxometric and photophysical properties of a new pH-responsive MRI contrast agent: the effect of other ligating groups on dissociation of a p-nitrophenolic pendant arm," *J. Amer. Chem. Soc.*, 126:9248-9256, 2004.

Zhang et al., "A novel pH-sensitive MRI contrast agent," *Angewandte Chemie, Intl. Ed.*, 38:3192-3194, 1999.

Zhang et al., "A paramagnetic CEST agent for imaging glucose by MRI," *J. Amer. Chem. Soc.*, 125:15288-9, 2003.

Zhang et al., "MRI thermometry based on PARACEST agents," *J. Amer. Chem. Soc.*, 127:17572-3, 2005.

\* cited by examiner

HYPERPOLARIZED 89-YTTRIUM AND METHODS RELATING THERETO

CROSS-REFERENCE TO RELATED APPLICATIONS

This applications claims the priority of U.S. Provisional Patent Application Ser. No. 61/104,487, filed Oct. 10, 2008, the entire disclosure of which is specifically incorporated herein by reference.

This invention was made with government support under grant numbers CA-115531, DK-058398 and RR-02584 awarded by the National Institutes of Health. The government has certain rights in the invention.

BACKGROUND OF THE INVENTION

1. Field of the Invention

The present invention generally relates to the fields of spectroscopy, medical imaging and imaging agents. More specifically, it relates to hyperpolarized $^{89}Y$ for use as nuclear magnetic resonance agents and magnetic resonance imaging agents.

2. Description of Related Art

Magnetic resonance imaging (MRI) is a technique often used in radiology to visualize the structure and function of the body, such as in neurological (brain), musculoskeletal, cardiovascular and oncological imaging (e.g., imaging of tumors). Conventional MRI techniques exploit the interaction of the intrinsic magnetic moment or spin of nuclei with an applied magnetic field. Nuclei whose spin is aligned with the applied magnetic field have a different energy state than nuclei whose spin is aligned opposed to the applied magnetic field. By applying a radio frequency radiation to the nuclei in a magnetic field, nuclei can be made to jump from a lower energy state to a higher energy state. The signals produced when the nuclei return to the lower energy state can then be measured, thereby providing information concerning the nature of the physical properties of the object being measured. In certain circumstances, the associated changed population difference can be converted into a considerable increase of the signal intensity by factors of up to several thousand—this is referred to as hyperpolarization. Hyperpolarization of nuclear spins can produce a dramatic increase in sensitivity for certain nuclei.

Dynamic nuclear polarization (DNP) is one method to achieve hyperpolarization. DNP results from transferring spin polarization from electrons to nuclei, thereby aligning the nuclear spins to the extent that electron spins are aligned. Although the idea of transferring spin polarization from electrons to nuclei by DNP to create a hyperpolarized sample has been around since the mid-1950's, applications of this technology for study of liquid samples have appeared only recently. In 2003, Ardenkjaer-Larsen et al. (2003) developed an automated method to polarize $^{13}C$ nuclei at low temperatures in the presence of a stable trityl radical, then bring the sample to room temperature very quickly to perform nuclear magnetic resonance (NMR) measurements (Ardenkjaer-Larsen et al. 2003; Golman et al., 2003). This method was most practical for long $T_1$ $^{13}C$ nuclei, such as non-protonated carbonyl or carboxyl carbons, in rapidly tumbling small molecules which yield NMR signal enhancements of 10,000-fold or higher. One of the more exciting applications of this technology was reported shortly thereafter by Golman et al. (2006a); Golman and Petersson (2006b) who demonstrated that it is practical to perform real time metabolic imaging of [1-$^{13}C$]pyruvate, [1-$^{13}C$]lactate and [1-$^{13}C$]alanine in live animals using $^{13}C$ chemical shift imaging.

As conventional MRI imaging agents, which are based on $^1H$, typically suffer from low sensitivity, identification of agents that may be hyperpolarized via DNP may offer a means to better map physiological parameters such as pH, temperature, and other indices of metabolism in vivo. MRI imaging of structural features of subjects, such as organs and tumors, may be improved using agents hyperpolarized through DNP. Commercial DNP devices derived from this technology offer new opportunities for imaging nuclei that have not ordinarily been considered possible in the past. Agents to employ in these devices for MRI are still being identified, perfected, and are in great demand.

SUMMARY OF THE INVENTION

The present invention is based on the discovery that $^{89}Y$ may be hyperpolarized and used in NMR studies as well as MRI analyses. In both contexts, hyperpolarized $^{89}Y$ offers increased sensitivities in comparison to known agents. In particular, hyperpolarized $^{89}Y$ may be employed as a contrast agent in mammalian MRI studies to diagnose and detect various abnormalities and conditions in subjects.

Accordingly, in one general aspect, the present invention contemplates a composition comprising a $^{89}Y$-containing agent, a radical, a glassing agent and water. $^{89}Y$ may be provided in its natural form, wherein the natural form comprises the $^{89}Y$ isotope. The $^{89}Y$-containing agent may comprise $^{89}Y^{3+}$, in certain embodiments. The $^{89}Y$-containing agent may be a salt or a complex that comprises $^{89}Y^{3+}$. Salts that comprise $^{89}Y^{3+}$ include, e.g., $^{89}YBr_3$ and $^{89}YCl_3$.

The $^{89}Y$-containing agent may comprise a $^{89}Y^{3+}$ complex of an acyclic polyamine based ligand, a macrocyclic polyamine based ligand, a pyclen based ligand, a tripodal ligand, a cryptand, or a texaphyrin.

As used herein, an acyclic amine based ligand is a ligand that is capable of chelating a yttrium ion by virtue of an acyclic compound that comprises at least two secondary or tertiary nitrogen atoms, wherein the two or more nitrogen atoms contribute to chelating the yttrium ion.

As used herein, a macrocyclic amine based ligand is a ligand that that is capable of chelating an yttrium ion by virtue of a macrocyclic compound that comprises at least three secondary or tertiary nitrogen atoms, wherein the three or more nitrogen atoms contribute to chelating the yttrium ion.

As used herein, a pyclen based ligand is a ligand that is capable of chelating a yttrium ion by virtue of a compound that comprises a macrocyclic amine fused to a pyridine ring and has at least four secondary or tertiary nitrogen atoms, wherein the four or more nitrogen atoms contribute to chelating the yttrium ion.

As used herein, a tripodal ligand is a ligand that is capable of chelating a yttrium ion by virtue of an acyclic compound that comprises at least one central secondary or tertiary nitrogen atoms and at least one pendant arm attached to the central nitrogen atom, wherein the central nitrogen atom contributes to chelating the yttrium ion.

As used herein, a cryptand is a ligand that is capable of chelating a yttrium ion by virtue of a compound that is at least dicyclic and comprises at least two secondary or tertiary nitrogen atoms, wherein the two or more nitrogen atoms contribute to chelating the yttrium ion.

As used herein, a texaphyrin is a ligand that is capable of chelating a yttrium ion by virtue of an macroheterocyclic compound that comprises at least five secondary or tertiary nitrogen atoms, wherein the five or more nitrogen atoms contribute to chelating the yttrium ion.

In certain embodiments, the $^{89}$Y-containing agent comprises a $^{89}$Y$^{3+}$-complex of an acyclic polyamine based ligand. Non-limiting examples of acyclic polyamine based ligands include compounds of formula (I):

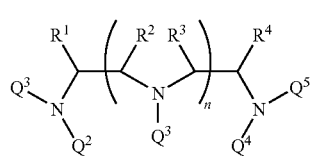

(I)

wherein: $Q^1$-$Q^5$ are each independently hydrogen, CHR$^5$COOR$^6$, CHR$^5$CONR$^6$R$^7$, CH$_2$CHR$^5$OH, CH$_2$CHR$^5$OR$^6$, CH$_2$CHR$^5$NR$^6$R$^7$, CHR$^5$P(O)R$^6$R$^7$, or CHR$^5$C(O)R$^6$, wherein: $R^1$-$R^7$ are each independently hydrogen, hydroxyl, or an amino acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and n=0, 1, or 2. In certain embodiments, $R^1$-$R^7$ are each independently hydrogen, hydroxyl, alkyl, cycloalkyl, alkoxy, hydroxyalkyl, oxoalkyl, carboxyalkyl, alkoxycarbonylalkyl, aminoalkyl, amidoalkyl, aryl, heteroaryl, aryloxy, nitroaryl, aminoaryl, amidoaryl, isothiocyanatoaryl, carboxyaryl, nitroaralkyl, aminoaralkyl, amidoaralkyl, isothiocyanatoaralkyl, carboxyaralkyl, amino acid or boronic acid containing group or may be taken with an adjacent R to form an additional carbon-carbon bond. In certain embodiments, the compound of formula (I) is further defined as ethylenediaminetetraacetic acid (EDTA), diethylenetriaminepentaacetic acid (DTPA), nitrobenzyl-diethylenetriaminepentaacetic acid, diethylenetriaminepentaacetic acid bis(methylamide) and triethylenetetraminehexaacetic acid (TTHA).

In certain embodiments, the $^{89}$Y-containing agent comprises a $^{89}$Y$^{3+}$-complex of a macrocyclic polyamine based ligand. Non-limiting examples of macrocyclic polyamine based ligands include compounds of formula (II):

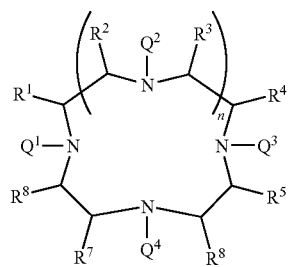

(II)

wherein: $Q^1$-$Q^4$ are each independently hydrogen, CHR$^9$COOR$^{10}$, CHR$^9$CONR$^{10}$R$^{11}$, CH$_2$CHR$^9$OH, CH$_2$CHR$^9$OR$^{10}$, CH$_2$CHR$^9$NR$^{10}$R$^{11}$, CHR$^9$P(O)R$^{10}$R$^{11}$, or CHR$^9$C(O)R$^{10}$, wherein: $R^1$-$R^{11}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and n=0, 1, or 2. In certain embodiments, $R^1$-$R^{11}$ are each independently hydrogen, hydroxyl, alkyl, cycloalkyl, alkoxy, hydroxyalkyl, oxoalkyl, carboxyalkyl, alkoxycarbonylalkyl, aminoalkyl, amidoalkyl, aryl, heteroaryl, aryloxy, nitroaryl, aminoaryl, amidoaryl, isothiocyanatoaryl, carboxyaryl, nitroaralkyl, aminoaralkyl, amidoaralkyl, isothiocyanatoaralkyl, carboxyaralkyl or amino acid containing group or may be taken with an adjacent R to form an additional carbon-carbon bond. Non-limiting examples of compounds of formula (II) include 1,4,7,10-tetraazacyclododecane-1,4,7,10-tetraacetic acid (DOTA), 1,4,7,10-tetraazacyclododecane-1,4,7-triacetic acid (DO3A), 10-hydroxypropyl-1,4,7,10-tetraazacyclododecane-1,4,7-triacetic acid (HP-DO3A), 1,4,7,10-tetraazacyclododecane-1,4,7,10-tetraacetic acid (tetraglycine amide) (DOTAGly$_4$), p-nitrobenzyl-1,4,7,10-tetraazacyclododecane-1,4,7,10-tetraacetic acid (NO$_2$Bn-DOTA), 1,4,7,10-tetraazacyclododecane-1,4,7,10-tetramethylenephosphonic acid (DOTP), 1,4,7,10-tetraazacyclododecane-α,α',α'',α'''-tetramethyl-1,4,7,10-tetraacetic acid (DOTMA), 1,4,7,10-tetraazacyclododecane-1,7-diacetic acid-4,10-dimethylenephosphonic acid (DO2A2P), 1,4,7-triazacyclononane-1,4,7-triacetic acid (NOTA) and 7-[2-[bis(carboxymethyl)amino]ethyl]-1,4,7-triazacyclononane-1,4-diacetic acid (NETA).

In certain embodiments, the $^{89}$Y-containing agent comprises a $^{89}$Y$^{3+}$-complex of a pyclen based ligand. Non-limiting examples of pyclen based ligands include compounds of formula (III):

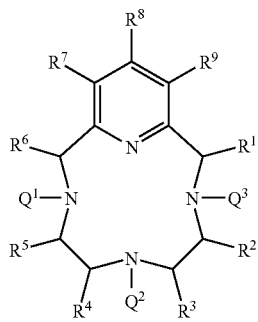

(III)

wherein: $Q^1$-$Q^3$ are each independently CHR$^{10}$COOR$^{11}$, CHR$^{10}$CONR$^{11}$R$^{12}$, CH$_2$CHR$^{10}$OH, CH$_2$CHR$^{10}$OR$^{11}$, CH$_2$CHR$^{10}$NR$^{11}$R$^{12}$, CHR$^{10}$P(O)R$^{11}$R$^{12}$, or CHR$^{10}$C(O)R$^{11}$, wherein: $R^1$-$R^{12}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond. In certain embodiments, $R^1$-$R^{12}$ are each independently hydrogen, hydroxyl, alkyl, cycloalkyl, alkoxy, hydroxyalkyl, oxoalkyl, carboxyalkyl, alkoxycarbonylalkyl, aminoalkyl, amidoalkyl, aryl, heteroaryl, aryloxy, nitroaryl, aminoaryl, amidoaryl, isothiocyanatoaryl, carboxyaryl, nitroaralkyl, aminoaralkyl, amidoaralkyl, isothiocyanatoaralkyl, carboxyaralkyl or amino acid containing group or may be taken with an adjacent R to form an additional carbon-carbon bond. Non-limiting examples of compounds of formula (III) include pyclen triacetic acid (P CTA, 3,6,9,15-tetraazabicyclo[9.3.1]pentadeca-1(15), 11,13-triene-3,6,9-triacetic acid), p-nitrobenzylpyclen triacetic acid, cyclohexylpyclen triacetic acid, pyclen trimethylenephosphonic acid and pyclen tri(methylenephosphonic acid monobutyl ester.

In certain embodiments, the $^{89}$Y-containing agent comprises a $^{89}$Y$^{3+}$-complex of a tripodal ligand. Non-limiting examples of tripodal ligands include compounds of formula (IV):

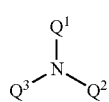

(IV)

wherein: $Q^1$-$Q^3$ are each independently CHR$^1$COOR$^2$, CHR$^1$CONR$^2$R$^3$, CH$_2$CHR$^1$OH, CH$_2$CHR$^1$OR$^2$, CH$_2$CHR$^1$NR$^2$R$^3$, CH$_2$CHR$^1$NCOR$^4$, CHR$^1$P(O)R$^2$R$^3$, CH$_2$CHR$^1$NCOR$^4$, or CHR$^1$C(O)R$^2$, wherein: R$^1$-R$^3$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; and R$^4$ is alkyl, aryl, heteroaryl, hydroxypyridonyl, hydroxypyrimidinonyl, or hydroxyisoquinolinonyl. In certain embodiments, R$^1$-R$^3$ are independently hydrogen, hydroxyl, alkyl, cycloalkyl, alkoxy, hydroxyalkyl, oxoalkyl, carboxyalkyl, alkoxycarbonylalkyl, aminoalkyl, amidoalkyl, aryl, heteroaryl, aryloxy, nitroaryl, aminoaryl, amidoaryl, isothiocyanatoaryl, carboxyaryl, nitroaralkyl, aminoaralkyl, amidoaralkyl, isothiocyanatoaralkyl, carboxyaralkyl, or amino acid containing group. In certain embodiments, R$^4$ is alkyl, cycloalkyl, hydroxyalkyl, carboxyalkyl, aryl, heteroaryl, hydroxyaryl, dihydroxyaryl, hydroxyheteroaryl, dihydroxyheteroaryl, hydroxypyridone, hydroxypyrimidinone or hydroxyisoquinolinone-containing group. Non-limiting examples of compounds of formula (IV) include nitrilotriacteic acid, nitrilotris(methylenephosphonic acid), N,N',N''-(nitrilotri-2,1-ethanediyl)tris[1,2-dihydro-3-hydroxy-1-methyl-2-oxo-4-pyridine-carboxamide], N,N',N''-(nitrilotri-2,1-ethanediyl)tris[1,6-dihydro-1-hydroxy-6-oxo-2-pyridinecarboxamide] and N,N'',N''''-(nitrilotri-2,1-ethanediyl)tris[2,3-dihydroxy-N'-(2-hydroxyethyl) 1,4-benzenedicarboxamide].

In certain embodiments, the $^{89}$Y-containing agent comprises a $^{89}$Y$^{3+}$-complex of a cryptand ligand. Non-limiting examples of cryptand ligands include compounds of formula (V):

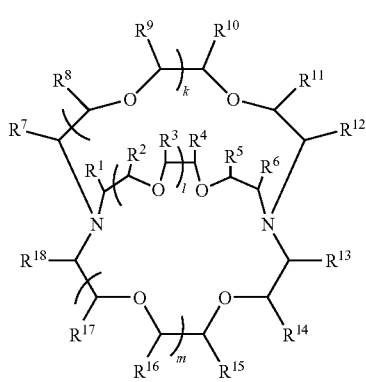

(V)

wherein: R$^1$-R$^{18}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and k, l and m are each independently =0, 1, or 2. In certain embodiments, R$^1$-R$^{18}$ are each independently hydrogen, hydroxyl, alkyl, cycloalkyl, alkoxy, hydroxyalkyl, carboxyalkyl, alkoxycarbonylalkyl, aminoalkyl, amidoalkyl, aryl, heteroaryl, aryloxy, nitroaryl, aminoaryl, amidoaryl, isothiocyanatoaryl, carboxyaryl, nitroaralkyl, aminoaralkyl, amidoaralkyl, isothiocyanatoaralkyl, carboxyaralkyl or amino acid containing group or may be taken with an adjacent R to form an additional carbon-carbon bond. Non-limiting examples of compounds of formula (V) include 4,7,13,16,21,24-hexaoxa-1,10-diazabicyclo[8.8.8]hexacosane (Cryptand [2.2.2]), 4,7,13,16,21-pentaoxa-1,10-diazabicyclo[8.8.5]tricosane (Cryptand[2.2.1]), dicyclohexylcryptand[2.2.2], dibenzocryptand[2.2.2], 4,7,13,16,21,24-hexaoxa-1,10-diazabicyclo[8.8.8]hexacosane-5-methanol and 4,7,13,16,21-pentaoxa-1,10-diazabicyclo[8.8.5]tricosane-5-methanol.

In certain embodiments, the $^{89}$Y-containing agent comprises a $^{89}$Y$^{3+}$-complex of a texaphyrin ligand. Non-limiting examples of texaphyrin ligands include compounds of formula (VI):

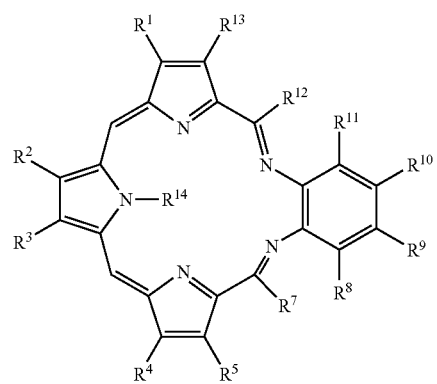

(VI)

wherein: R$^1$-R$^{13}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and R$^{14}$ is hydrogen or lower alkyl, lower alkenyl, lower acyl or a substituted version of any of these groups. In certain embodiments, R$^1$-R$^{13}$ are each independently hydrogen, hydroxyl, alkyl, cycloalkyl, alkoxy, hydroxyalkyl, hydroxyalkoxy, oxoalkyl, carboxyalkyl, alkoxycarbonylalkyl, aminoalkyl, amidoalkyl, aryl, heteroaryl, aryloxy, nitroaryl, aminoaryl, amidoaryl, isothiocyanatoaryl, carboxyaryl, nitroaralkyl, aminoaralkyl, amidoaralkyl, isothiocyanatoaralkyl, carboxyaralkyl, amino acid or boronic acid containing group or may be taken with an adjacent R to form an additional carbon-carbon bond. Non-limiting examples of compounds of formula (VI) include 9,10-diethyl-20,21-dimethoxy-4,15-dimethyl-8,11-imino-3,6:16,13-dinitrilo-1,18-benzodiaza-cycloeicosine-5,14-dipropanol, 9,10-diethyl-20,21-bis(3-hydroxypropoxy)-4,15-dimethyl-8,11-imino-3,6:16,13-dinitrilo-1,18-benzodiazacycloeicosine-5,14-dipropanol and 9,10-diethyl-20,21-bis[2-[2-(2-methoxyethoxy)ethoxy]ethoxy]-4,15-dimethyl-8,11-imino-3,6:16,13-dinitrilo-1,18-benzodiazacycloeicosine-5,14-dipropanol.

Radicals that may be employed in compositions and methods of the present invention are well-known in the art. Generally speaking, the radicals should be sufficiently persistent to allow for isolation, characterization and use in hyperpolarization. Typically, the radical is a stable, water-soluble radical with an ESR linewidth between about 44 MHz and about 300 MHz at a magnetic field strength of about 3.35 Tesla. Definitions of "stable" and "water-soluble" are provided herein. Such radicals may be trityl radicals or nitroxide radicals, for example. In certain embodiments, the radical is a trityl radical. Trityl radicals are well-known in the art. Non-limiting examples of trityl radicals include tris{8-carboxyl-2,2,6,6-tetra[2-(1-hydroxyethyl)]-benzo(1,2-d:4,5-d)bis(1,3)dithiole-4-yl}methyl sodium salt, OX63 and Finland. Other non-limiting examples of trityl radicals are described in WO 98/39277, WO 97/09633, WO 96/39367 and WO 91/12024, each of which is incorporated herein by reference in its entirety. Trityl radicals also include ones in which the aromatic hydrogens are replaced with zero spin nuclei (e.g., $^{12}C$, $^{32}S$, $^{16}O$), such that the resulting radicals have only one narrow EPR line, such as OX63 and Finland.

The radical may be a nitroxide radical, such as TEMPONE, TEMPO, or TEMPOL. In certain embodiments, the nitrogen of the nitroxide radical is further defined as $^{15}N$ and the nitroxide radical comprises at least one deuterium atom. In certain embodiments, the nitroxide radical is further defined as $[^{15}N]$-TEMPONE-$d_{16}$ or $[^{15}N]$-2,5-di(tert-butyl)-(3,4)-dimethoxycarbonyl pyrroloxyl-$d_2$. Non-limiting examples of nitroxide radicals are sold by Aldrich (see, e.g., world wide web at sigmaaldrich.com/catalog/search/TablePage/16280169). The radical may, in certain embodiments, be further defined as a radical that comprises any of the following moieties: pentaarylcyclopentadienyl, bisphenylenediallyl (BDPA), galvinoxyl, or diphenylpicrylhydrazyl (DPPH). The radical may, in certain embodiments, be further defined as a paramagnetic transition metal salt or complex, such as chromium(V)-2-ethyl-2-hydroxybutanoate (Cr(V)-ehba).

Glassing agents, defined below, that may be employed in hyperpolarization studies are well-known in the art. Glassing agents typically are chosen such that the radical dissolves in the glassing agent. The glassing agent may be, for example, an alcohol having a molecular weight of about 250 g/mol or less. In certain embodiments, the molecular weight of the alcohol is about 250, 240, 230, 220, 210, 200, 190, 180, 170, 160, 150, 140, 130, 120, 110, 100, 90, 80, 70, 60, 50, or 40 g/mol or less, or any range derivable therein. In certain embodiments, the alcohol is further defined as glycerol, methanol, ethanol, or propanediol. The glassing agent may be dimethylsulfoxide, in certain embodiments. Combinations of glassing agents are also contemplated. Other non-limiting examples of glassing agents are described in U.S. Application No. 2006/0173282, incorporated herein by reference.

As used herein, "water" may be $H_2O$ or $D_2O$.

In any composition described herein, the ratio of glassing agent to water may range from about 10:90 to about 90:10. In certain embodiments, the ratio may be about, at most about, or at least about 10:90, 20:80, 30:70, 40:60, 50:50, 60:40, 70:30, 80:20, or 90:10, or any range derivable therein. In particular embodiments, the ratio of glassing agent to water ranges from about 40:60 to about 60:40. In certain embodiments, wherein the ratio is about 50:50.

A composition of the present invention may be a liquid composition. In certain embodiments, a composition may be a frozen composition. Any composition described herein may be a hyperpolarized composition, wherein the term "hyperpolarized" is defined below.

Methods of preparing compositions, mixtures and samples of the present invention are also contemplated, such as a method of preparing hyperpolarized $^{89}Y$ comprising hyperpolarizing a mixture of a $^{89}Y$-containing agent, a radical, a glassing agent and water. Any of these ingredients may be employed in any combination described herein. Methods of hyperpolarization are well-known in the art. One example is a "brute-force" method, wherein the temperature of the sample is lowered to the micro-Kelvin range via the use of a dilution refrigerator and a mixture of $^3He$ and $^4He$. However, this method is difficult and expensive to employ. Another method of hyperpolarization comprises dynamic nuclear polarization (DNP), which is described in further detail herein. Yet a further method of hyperpolarization comprises cross polarization (CP), which is described in further detail herein. Accordingly, methods of the present invention contemplate subjecting a mixture, sample, or composition, as described herein, to dynamic nuclear polarization. Such methods may further comprise freezing the mixture. Any method described herein may comprise DNP or CP, and may further comprise a freezing step.

Another general embodiment of the present invention contemplates a method comprising detecting the presence of hyperpolarized $^{89}Y$ in a sample by nuclear magnetic resonance spectroscopy. The sample may further comprise a radical, a glassing agent, and/or water, as described herein. In certain embodiments, a sample comprises an $^{89}Y$-containing agent, a radical, a glassing agent and water. Preparation of a sample comprising hyperpolarized $^{89}Y$ may comprise, for example, hyperpolarizing a mixture of a $^{89}Y$-containing agent, a radical, a glassing agent and water.

In certain embodiments, the difference in time between the completion of hyperpolarizing of a mixture, sample, or composition in a method of the present invention and the detection of hyperpolarized $^{89}Y$ in the mixture, sample, or composition is less than 5 minutes. In certain embodiments, the difference is at most about or about 5, 4.5, 4, 3.5, 3, 2.5, 2, 1.5, 1, or 0.5 minutes or less, or any range derivable therein. In certain embodiments, the difference in time is less than 1 minute. In certain embodiments, the difference in time is 30 seconds or less.

A method comprising administering to a subject an effective amount of hyperpolarized $^{89}Y$ is also contemplated by the present invention. Also contemplated by the present invention is a method comprising detecting the presence of hyperpolarized $^{89}Y$ in a subject by magnetic resonance imaging (MRI). In this or any method described herein regarding MRI, the method may further comprise obtaining an image of the subject.

Other embodiments of the present invention contemplate a method comprising: (a) administering to a subject an effective amount of a composition comprising hyperpolarized $^{89}Y$; and (b) detecting the presence of hyperpolarized $^{89}Y$ in the subject by magnetic resonance imaging. The composition may be any composition described herein. The composition may further comprise, for example, water or a glassing agent. This or any other method described herein may further comprise a method of preparing a composition comprising an effective amount of hyperpolarized $^{89}Y$. Such methods may comprise, for example, (a) combining a $^{89}Y$-containing agent, a radical, a glassing agent and water to form a mixture; (b) hyperpolarizing the mixture; and (c) removing the radical from the mixture to form a composition that comprises an effective amount of hyperpolarized $^{89}Y$. As discussed herein, the difference in time between the completion of step (b) and the detection of hyperpolarized $^{89}Y$ in the subject may be, e.g., less than 5 minutes. In certain embodiments, the difference is at most about or about 5, 4.5, 4, 3.5, 3, 2.5, 2, 1.5, 1, or 0.5 minute or less, or any range derivable therein. In certain embodiments, the difference in time is less than 1 minute. In certain embodiments, the difference in time is 30 seconds or less. Compositions of the present invention may be administered to subjects via injection, for example.

As noted herein, methods of the present invention that comprise MRI may comprise obtaining an image of a subject. In the context of MRI imaging, hyperpolarized $^{89}$Y may detected in any part of a subject amenable to MRI imaging, as known to those of skill in the art. In certain embodiments, hyperpolarized $^{89}$Y is detected in an organ. Non-limiting examples of organs include the brain, eye, bone, tongue, thymus, heart, breast, colon, lung, pancreas, spleen, kidney, thyroid, bladder, liver, stomach, small intestine, large intestine, rectum, uterus, ovary, scrotum, testis and prostate. Hyperpolarized $^{89}$Y may be detected, for example, in or on a lymph node, or in the central nervous system. In certain embodiments, hyperpolarized $^{89}$Y is detected in a tumor, such as a cancerous tumor.

As used herein, a "glassing agent" refers to a liquid that, when combined with water, prevents ice crystals from forming such that an amorphous material results (i.e., there is no long-range order in the material). Detection of ice crystals may be performed using methods known to those of skill in the art, such as via x-ray crystallography.

By hyperpolarization, it is meant that a sample is polarized to a level over that found at room temperature and 1 Tesla (T). In certain embodiments, the sample is polarized to a polarization degree in excess of about 0.1%, 1%, 10%, or higher, or any range derivable therein. A hyperpolarized sample, hyperpolarized composition, or hyperpolarized $^{89}$Y is a sample, composition or $^{89}$Y atom, respectively, that has been subjected to this hyperpolarization. The temperature employed should be very low, e.g., about 100 K or less. In certain embodiments, the temperature is about or at most about 4, 2, 1.4, 1.2, or 1 K or less. In particular embodiments, the temperature is about 1.2 K. In other particular embodiments, the temperature is about 1 K.

As used herein, the term "stable," when used to describe radicals of the present invention, refers to a radical that exhibits a lifetime of 24 hours or more.

As used herein, "water soluble" refers to a solubility in water of at least 0.5 g per 100 g of water at 20° C.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. Compositions of the present invention that are administered to subjects should be pharmaceutically acceptable.

The term "effective," as that term is used in the specification and/or claims (e.g., "an effective amount"), means adequate to accomplish a desired, expected, or intended result.

As used herein, the term "subject" refers to a living mammalian organism, such as a human, monkey, cow, sheep, goat, dogs, cat, mouse, rat, and guinea pig. In certain embodiments, the subject is a primate. Non-limiting examples of human subjects are adults, juveniles, infants and fetuses.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention overcomes deficiencies of the prior art by providing hyperpolarized $^{89}$Y that may be used in, for example, NMR spectroscopy and MRI imaging. Spectroscopic detection and imaging sensitivities using hyperpolarized $^{89}$Y may be improved over other methods, allowing for more accurate NMR spectrums and MRI images to be obtained. Regarding MRI images in particular, such improved sensitivity allows for better patient diagnoses and, subsequently, better therapy management.

A. Dynamic Nuclear Polarization

Dynamic nuclear polarization to achieve high nuclear polarizations followed by fast dissolution to obtain narrow liquid state linewidths has already begun to revolutionize $^{13}$C imaging in vivo and $^{13}$C NMR detection in vitro, enabling a variety of studies previously unattainable with thermally polarized nuclei (Ardenkjaer-Larsen et al., 2003). DNP as a technique was first developed in the 1950's (Overhauser, 1953) and subsequently was primarily used to produce highly polarized solid targets for high energy physics studies (Abragam and Goldman, 1982). DNP continued to be used to enhance the sensitivity of solid state NMR studies throughout the intervening period of 1960-2004, but it was not until this time that the fast dissolution technique was developed by Golman and co-workers, as discussed above (Ardenkjaer-Larsen et al., 2003). In their studies, the extremely low temperatures and high magnetic field strength, 3.35 Tesla, served to produce electron polarizations on the order of 92-95%. This high polarization was transferred to the nuclei by microwave irradiation at ~94 GHz, the electron Larmor frequency at 3.35 T. However, the key to the success of the new method was a dissolution wand that mated to the top of the polarization chamber, injecting a bolus of boiling solvent which served to melt the frozen, hyperpolarized solid and transport it out of the low field DNP magnet to a waiting, high field detection magnet.

Since the initial publication of this method, the technique has enjoyed increasingly widespread use (Day et al., 2007; Golman et al., 2008; Kurhanewicz et al., 2008). In 2007, Oxford Instruments Molecular Biotools (OIMB) began marketing a commercial version of the fast dissolution (fd) DNP device (named HyperSense) that automates the dissolution process. To this point, the HyperSense has been used to great effect studying metabolism and NMR phenomena essential to the quantitative measurement of metabolic flux in vivo (Merritt et al., 2007a; Merritt et al., 2007b).

Figure 1:
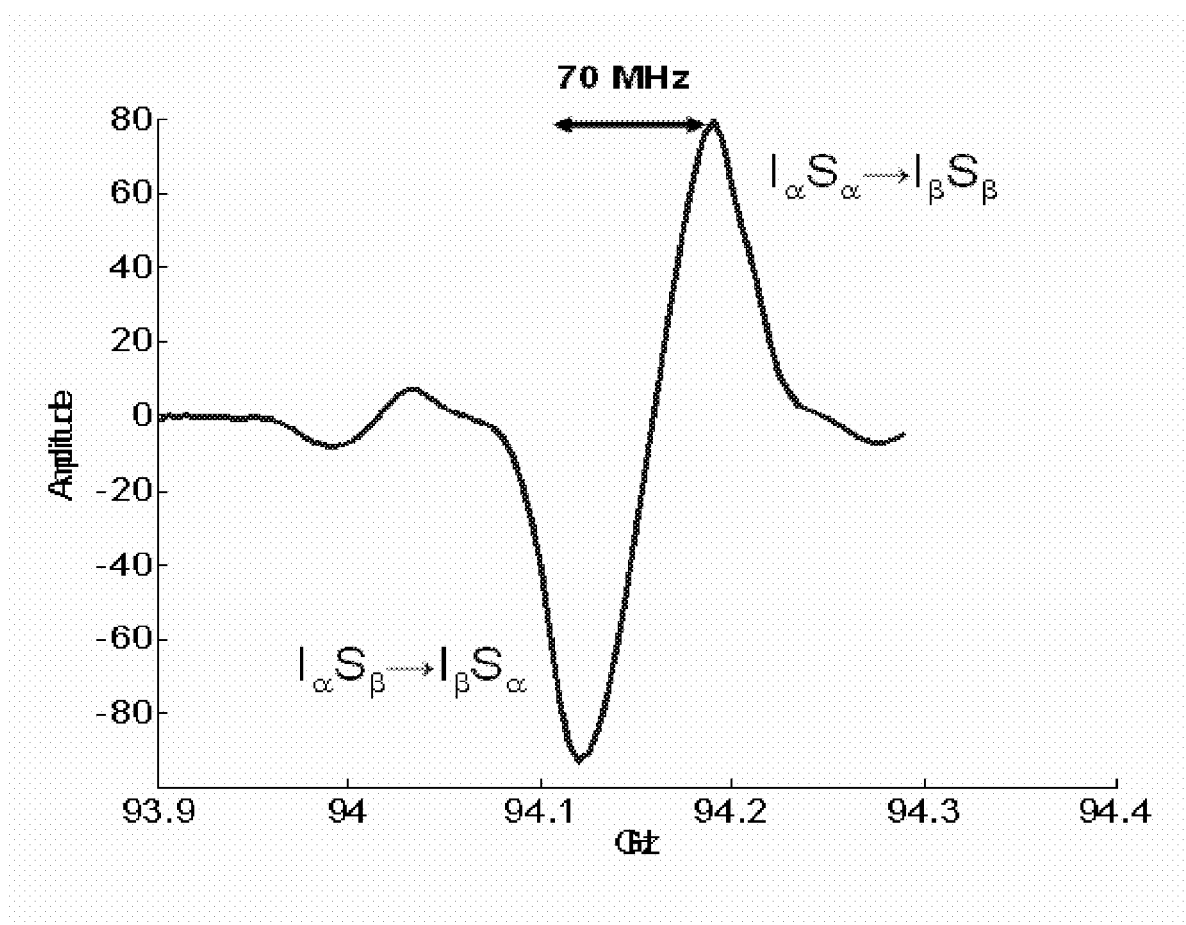
FIG. 1: NMR signal enhancement as a function of frequency when performing DNP with $^{13}$C pyruvate and the trityl radical. The enhancement is primarily due to the solid effect, as evidenced by the $2*\omega_C$ splitting. The extra peaks around 94 GHz arise from 4 spin effects in the 99% labeled pyruvate.

DNP effectively transfers polarization from a high gyromagnetic ratio (γ) source, usually an electron, to a lower γ nucleus. The transfer is most often accomplished through one of two mechanisms, although an admixture of mechanisms is possible in certain cases. The solid effect (SE) depends upon strong dipolar coupling between a spin pair composed of an electron and a nucleus. Due to a perturbation of the Zeeman energy levels by the strong hyperfine coupling, normally forbidden transitions are allowed. The double quantum transitions $I_\alpha S_\alpha \to I_\beta S_\beta$ and $I_\alpha S_\alpha \to I_\beta S_\alpha$ can be pumped by irradiation at the electron Larmor frequency±the nuclear frequency. The nuclear enhancement produced by the solid effect shows an antiphase character, such as that as shown in FIG. 1. At steady state under microwave excitation, the total enhancement should be equal for the positive and negative lobes. SE is effective when the width of the electron paramagnetic resonance (EPR) line is less than or equal to the nuclear Larmor frequency. Since the transitions in SE are forbidden, effective enhancements usually have a strong dependence on incident microwave power.

The other mechanisms commonly seen at intermediate field strengths (3.35 Tesla) are the cross effect (CE) and the thermal mixing effect (TM). Both of these mechanisms are three spin effects involving two electrons and a nucleus, and therefore do not depend upon forbidden transitions. Consequently, both CE and TM DNP usually demand less power than the solid effect. In contrast to the solid effect, CE and TM take place when the EPR linewidth is greater than the nuclear Larmor frequency (Abragam and Goldman, 1982). The general condition is that $\omega_0^{e1} - \omega_0^{e2} = \omega_0^{Nuc}$, or that the difference in frequency for the two electron spins is equal to the nuclear Larmor frequency.

CE functions when the EPR line is inhomogeneously broadened, and is achievable mainly in the context of studies with bi-radicals and high magnetic field strengths (Hu et al., 2004). TM occurs when the EPR resonance is homogeneously broadened. Microwave irradiation at a single frequency to either side of the center of the EPR resonance causes differential cooling across the dipolar coupled electron spin bath. As the electron spin system tries to return to thermal equilibrium dipolar flip-flops occur between the coupled electron spins. However, the difference in the energy between upfield and downfield electron spins must be accounted for, so when two electrons at different energies flip, a coupled nuclear species makes up for the difference and flips at the same time. Once again, this mechanism produces an antiphase enhancement curve as a function of microwave irradiation frequency, though this time the splitting between the positive and negative enhancement lobes is only the nuclear Larmor frequency (Abragam and Goldman, 1982). TM can be explained in a thermodynamic formalism as the interaction of a cold electron spin bath with a warmer nuclear bath (Abragam and Goldman, 1982). Therefore, deuteration of any surrounding molecules in the matrix will lower the nuclear spin heat capacity of the frozen matrix, making higher absolute polarizations available for the heteronuclei of interest. Intrinsic to TM is the understanding that electron-electron dipolar flip-flops are possible. Therefore, higher concentrations of radical are often used, with 30-40 mM being typical (Comment et al., 2007).

Both CE and TM DNP mechanisms depend upon nuclear spin diffusion to propagate polarization throughout the entire macroscopic sample. The canonical model is of a nearest neighbor nuclear spin becoming polarized by either mechanism. Nuclear spin diffusion is the analogue to the electron dipolar flip-flops, and proceeds at a rate that proceeds as $\gamma^2$. Therefore, DNP of proton spins is kinetically efficient compared to other nuclei. Previous results indicate that the proton spin bath can become fully polarized in less than one minute (Maly et al., 2008). It is of note that since both mechanisms depend upon dipolar flip-flops of either the electron or nuclear spin bath, or both, it is absolutely necessary that the polarized samples be formed as a glass. Micro-crystallization causes fractures within the sample, preventing the close contact necessary for effective dipolar couplings between the spins and the formation of a macroscopic spin bath. Therefore, most DNP samples are prepared in a water matrix with a glassing agent, such as glycerol or ethanol, or other glassing agents discussed herein.

B. Cross Polarization

Hyperpolarization followed by fast dissolution provides tremendous gains in SNR in both NMR and MRI studies, but a fundamental limitation in its application is the $T_1$ decay of the magnetization in the liquid state (Ardenkjaer-Larsen et al., 2003). Production of hyperpolarized (HP) $^{89}Y$ samples is handicapped by the long times (2.5 hours) needed for magnetization transfer between the free radical that is part of the sample matrix and the $^{89}Y$ nucleus. This decay constricts the allowable time interval between the dissolution and data acquisition steps in an HP experiment. $^{89}Y$ offers a potential solution to this problem as it has been shown that it can be hyperpolarized and exhibits exceptionally long $T_1$'s in solution (Merritt et al., 2007). $^{89}Y$'s primary drawback is its inherently low gyromagnetic ratio (approximately 5% of 1H), which reduces the total polarization available by dynamic nuclear polarization (DNP), as well as the rate of polarization buildup under microwave irradiation. To overcome this slow polarization rate, the proton spin bath in the solid state could initially be hyperpolarized, after which the polarization would be transferred via dipolar coupling to $^{89}Y$ spins via a cross polarization (CP) scheme.

Figure 5:
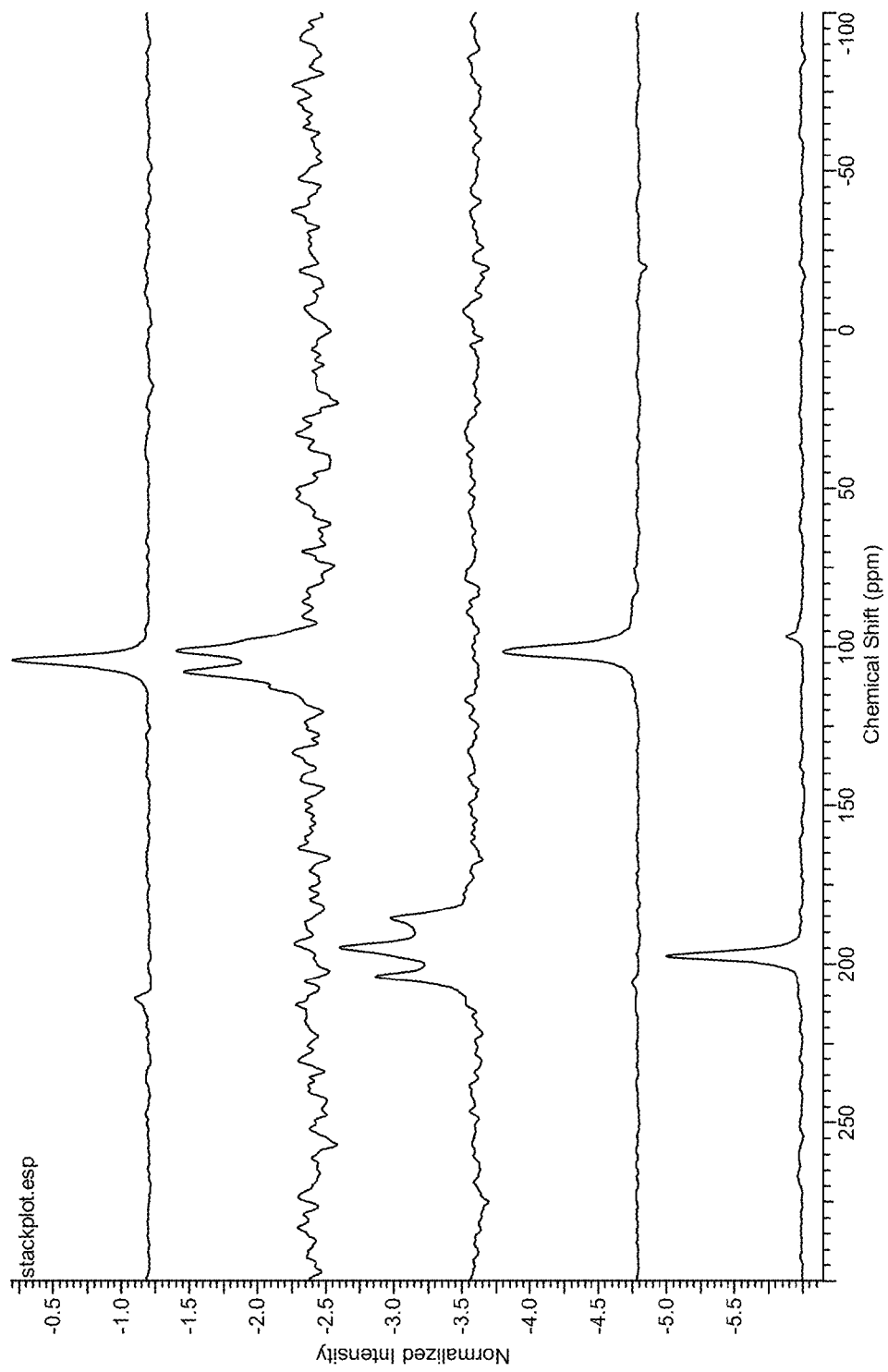
FIG. 5: Cross polarization magic angle spinning spectra of Y(DOTA) made with 5 different counter-ions. From top to bottom, the ions are ammonium, sodium, tetra-methyl ammonium, potassium, and tetra-butyl ammonium. The spinning spend was 5 kHz and the CP contact times were 12 milliseconds. Choice of counter ion changes the conformation of the Y(DOTA), resulting in the observation of two distinct shift. Additional splitting in the resonances for the sodium and tertra-methyl ammonium samples is due to slight differences in micro environment in the lyophilized samples.
Figure 6:
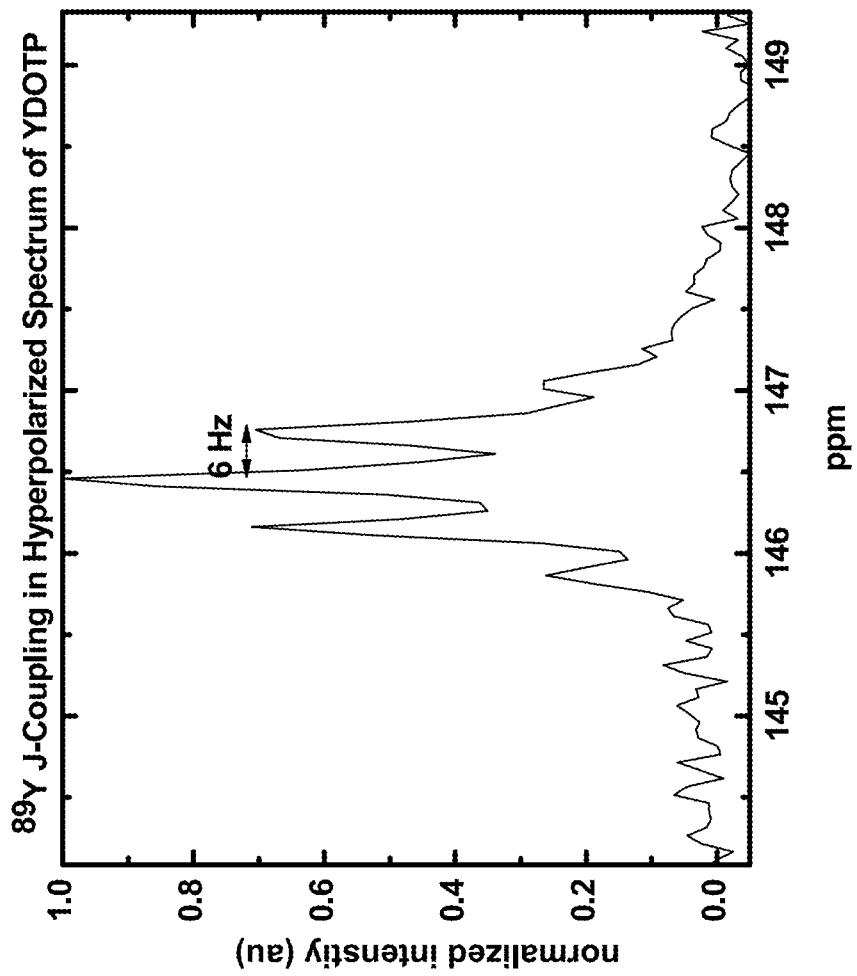
FIG. 6: $^{89}$Y spectrum of hyperpolarized YDOTP at pH seven (not buffered solution) at 25 C.°.
Figure 7:
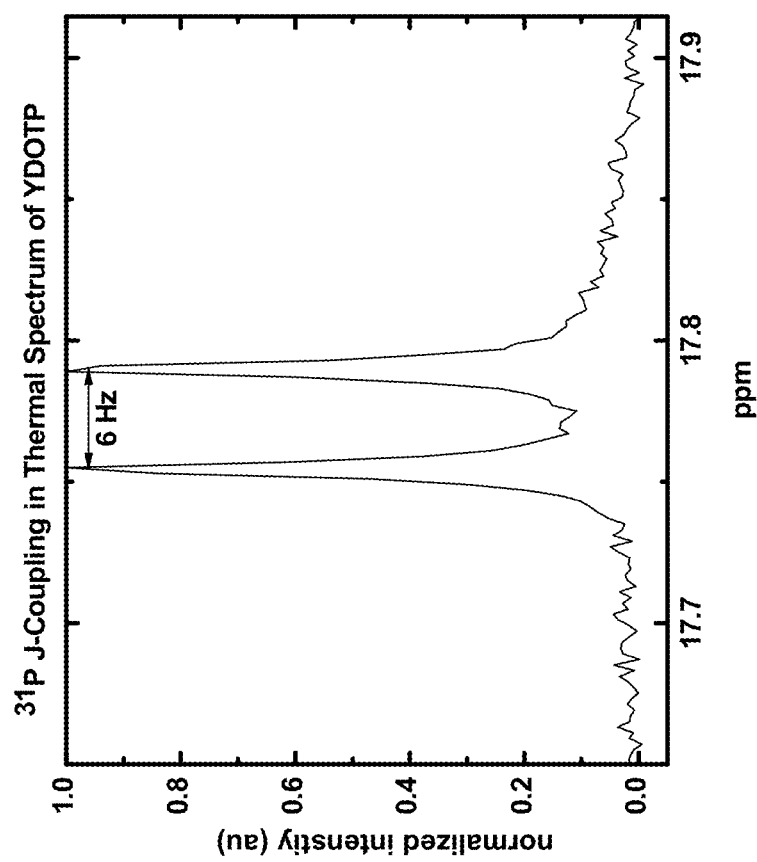
FIG. 7: $^{31}$P NMR spectrum of YDOTP at pH seven (not buffered solution) at 25 C.°.

This alternative paradigm for producing HP $^{89}Y$ samples is to first transfer magnetization from the free radicals to the protons then use the cross polarization (CP) method to transfer polarization from the protons to the $^{89}Y$ nucleus. This can be accomplished by using any free radical: trityl, tempo, tempone, bdpa, etc. and any variant of the cross polarization technique, which uses applied alternating applied magnetic fields induced inside an NMR coil surrounding the sample at matched nutation frequencies to each nucleus simultaneously. This transfer can be performed at constant amplitude, with an increasing ramp of the amplitudes, or using an adiabatic amplitude or phase modulated scheme. This method can be used with magnetic field strengths from 0.05 T to 30 T, with temperatures from 298 K to 0 K, with $B_1$ field strengths from 1 kHz to 1 MHz, and CP times from 10 us to 100 ms. This change in methodology should allow samples to be produced on a 2 minute time scale. Investigations into $^1H$-$^{89}Y$ CP at room temperature in a 9.4 T system are presented herein. For the case of Y(DOTA)-complexes formed with a protonated counter-ion, the data shows $^{89}Y$ sensitivity can indeed by enhanced by CP, even when carried out without DNP, and that yttrium chemical shift anisotropies are relatively small (FIG. 5). Small anisotropies mean that CP is likely to be effective for many samples in general without undue demands upon the $B_1$ levels needed to perform the experiment.

C. $^{89}Y$

Yttrium is a chemical element with symbol Y and atomic number 39. It is a silvery-metallic transition metal chemically similar to the lanthanoids and has historically been classified as a rare-earth element. Yttrium is almost always found combined with the lanthanoids in rare-earth minerals and is never found in nature as a free element. Its only stable isotope, $^{89}Y$, is also its only naturally-occurring isotope. $^{89}Y^{3+}$ is the only known yttrium ion.

$^{89}Y$ is difficult to detect by NMR at thermal Boltzmann polarization levels due to its small magnetic moment, low receptivity and long $T_1$ relaxation times. Only one $^{89}Y$ NMR study was reported prior to the 70's (Brun et al., 1949). With the advent of Fourier transform (FT) spectrometers, a few more reports appeared demonstrating that $^{89}Y$ salts have unusually long $T_1$ values and are concentration dependent (Hassler et al., 1977; Adam et al., 1979)). More interestingly, Levy, et al. (1980) were first to show that complexation of $^{89}Y^3$ with crown ethers of various ring size resulted in lengthening of $T_1$ about 4-fold over that measured for salts dissolved in DMSO. In 1990, Holz and Horrocks used $^{89}Y^{3+}$ as a $Ca^{2+}$ surrogate and reported that the chemical shift of various chelated forms of $Y^{3+}$ varies widely, ranging from 36.6 ppm when bound at the EF site of parvalbumin to 129.6 ppm in Y(EDTA) (Holz and Horrocks, 1990). This was the first demonstration that the chemical shift of $^{89}Y^{3+}$ complexes could be used as a probe of the coordination environment of the ion.

The present inventors are the first to demonstrate that $^{89}Y$ may be hyperpolarized. As described herein, the inventors performed DNP studies of $Y^{3+}$ complexes using a commercial polarizer, demonstrating that hyperpolarization of $^{89}Y$ is feasible with currently available commercial hardware. The wide chemical shift range for $^{89}Y$ means that contrast agents containing this element that are sensitive to a variety of biological/chemical milieu could serve as exquisite sensors of important biological events and of structural features in subjects.

D. Chemical Definitions

As used herein, "hydrogen" means —H; "hydroxy" or "hydroxyl" means —OH; "oxo" means =O; "carboxy" means —CO$_2$H; "halo" means independently —F, —Cl, —Br or —I; "amino" means —NH$_2$; "amido" means —C(O)NH$_2$; "nitro" means —NO$_2$; "cyano" means —CN; "azido" means —N$_3$; "mercapto" means —SH; "thio" means =S.

The term "alkyl" when used without the "substituted" modifier refers to a non-aromatic monovalent group, having a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tent-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group, having a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$. Alkyl groups contain 1-10 carbon atoms. In certain embodiments, "lower alkyl" groups are contemplated, which contain 1-3 carbon atoms.

Alkyl groups comprising one or more hydroxy groups, and no other substituents besides hydrogen and the hydroxy group(s), are also contemplated, and are termed "alcohols". Alcohols contain 1-10 carbon atoms. In certain embodiments, "lower alcohol" groups are contemplated, which contain 1-3 carbon atoms. An "oxoalkyl" group refers to an alkyl group that comprises a =O group—more particularly, a C=O group.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

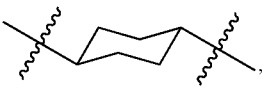 [SMILES: *C1CCC(*)CC1]

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—. Alkanediyl groups contain 1-10 carbon atoms. In certain embodiments, "lower alkanediyl" groups are contemplated, which contain 1-3 carbon atoms.

The term "alkenyl" when used without the "substituted" modifier refers to a monovalent group, having a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "substituted alkenyl" refers to a monovalent group, having a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups. Alkenyl groups contain 1-10 carbon atoms. In certain embodiments, "lower alkenyl" groups are contemplated, which contain 1-3 carbon atoms.

The term "aryl" when used without the "substituted" modifier refers to a monovalent group, having an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH═CH$_2$ (vinylphenyl), —C$_6$H$_4$CH═CHCH$_3$, —C$_6$H$_4$C≡CH, —C$_6$H$_4$C≡CCH$_3$, naphthyl, and the monovalent group derived from biphenyl. The term "substituted aryl" refers to a monovalent group, having an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$OH, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$. Aryl groups contain 6-12 carbon atoms. In certain embodiments, "lower aryl" groups are contemplated, which contain 6-7 carbon atoms.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenyl-carbonyl-methyl), 2-chloro-2-phenyl-ethyl, chromanyl where the point of attachment is one of the saturated carbon atoms, and tetrahydroquinolinyl where the point of attachment is one of the saturated atoms. Aralkyl groups contain 6-14 carbon atoms. In certain embodiments, "lower aralkyl" groups are contemplated, which contain 7-9 carbon atoms.

The term "heteroaryl" when used without the "substituted" modifier refers to a monovalent group, having an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group, having an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P. Heteroaryl groups contain 1-12 carbon atoms. In certain embodiments, "lower heteroaryl" groups are contemplated, which contain 1-5 carbon atoms.

The term "acyl" when used without the "substituted" modifier refers to a monovalent group, having a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group, having a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$C$_6$H$_5$, CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups. Acyl groups contain 1-10 carbon atoms. In certain embodiments, "lower acyl" groups are contemplated, which contain 1-3 carbon atoms.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "aryloxy", "heteroaryloxy", and "acyloxy", when used without the "substituted" modifier, refer to groups, defined as —OR, in which R is aryl, heteroaryl, and acyl, respectively, as those terms are defined above. When any of these terms is modified by "substituted," it refers to the group —OR, in which R is substituted aryl, heteroaryl, and acyl, respectively.

The term "amino acid" refers to any of the naturally occurring amino acids, as well as synthetic analogs (e.g., D-stereoisomers of the naturally occurring amino acids, such as D-threonine) and derivatives thereof. L-stereoisomers are also specifically encompassed by the present invention. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), heteroatom-substituted alkyl (e.g., as in threonine, serine, methionine, cysteine, aspartic acid, asparagine, glutamic acid, glutamine, arginine, and lysine), arylalkyl (e.g., as in phenylalanine and tryptophan), heteroatom-substituted arylalkyl (e.g., as in tyrosine), and heteroatom-substituted arylalkyl (e.g., as in histidine). Unnatural amino acids are also known in the art, as set forth in, for example, Williams (1989); Evans et al. (1990); Pu et al. (1991); Williams et al (1991); and all references cited therein. The present invention includes the side chains of unnatural amino acids as well. Amino acids comprising an additional methylene group in their backbone are often called β-amino acids; such amino acids are also encompassed by the present invention.

The term "boronic acid" refers to an alkyl or aryl substituted boric acid that contains a carbon-boron bond and derivatives of thereof.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

E. Composition Preparations and Uses

Samples, mixtures and compositions (collectively called "compositions") of the present invention that comprise $^{89}$Y typically comprise a $^{89}$Y-containing agent, a radical, a glassing agent and water. These ingredients are described elsewhere in this application. These compositions, with or without further manipulation, may be used in NMR or MRI studies. Compositions of the present invention, including pharmaceutical compositions, may comprise $^{89}$Y that is hyperpolarized or not hyperpolarized. Moreover, compositions may comprise $^{89}$Y-containing agent, a glassing agent and water.

Persons of skill in the art are well aware of NMR methods for detecting $^{89}$Y, and examples of detecting hyperpolarized $^{89}$Y are described herein. It is to be noted that the time between hyperpolarization of $^{89}$Y to the NMR detection of hyperpolarized $^{89}$Y in methods discussed herein should be about five minutes or less. Detection of hyperpolarized $^{89}$Y, for example, confirms to a skilled artisan that hyperpolarized $^{89}$Y was properly prepared, and that such preparation methods may be employed, for example, to prepare a sample for MRI imaging.

For MRI studies of a subject, the radical employed in hyperpolarizing $^{89}$Y is typically removed before a composition comprising hyperpolarized $^{89}$Y is administered. Other agents in the composition may be removed as well following hyperpolarization, if desired, keeping in mind the period of about five minutes or less between hyperpolarization and detection of $^{89}$Y. One method to remove a radical, for example, is to use a C$_{18}$ column, as is known in the art.

A composition of the present invention may be purified and/or dialyzed to remove undesired small molecular weight molecules or lyophilized for more ready formulation into a desired vehicle, where appropriate. Such methods are well-known in the art, and will typically take place before hyperpolarization so as not to lengthen the time between hyperpolarization and detection of hyperpolarized $^{89}$Y.

A composition of the present invention may be administered alone, or may be administered with a pharmaceutically acceptable carrier selected on the basis of the chosen route of administration and standard pharmaceutical practice. Such compositions are referred to as "pharmaceutical compositions." The phrases "pharmaceutically or pharmacologically acceptable" refer to molecular entities and compositions that do not produce an adverse, allergic or other untoward reaction when administered to an animal, such as, for example, a human, as appropriate. Moreover, for animal (e.g., human) administration, it will be understood that compositions should meet sterility, pyrogenicity, general safety and purity standards as required by the FDA's Center of Drug Evaluation and Research.

As used herein, "pharmaceutically acceptable carrier" includes any and all solvents, dispersion media, surfactants, antioxidants, preservatives (e.g., antibacterial agents and antifungal agents, including parabens (e.g., methylparabens, propylparabens), chlorobutanol, phenol, sorbic acid, thimerosal, or combinations thereof), isotonic agents, salts, drugs, drug stabilizers, gels, binders, excipients, disintegration agents, lubricants, dyes, and similar materials and combinations thereof, as would be known to one of ordinary skill in the art (see, for example, Remington's Pharmaceutical Sciences, pp 1289-1329, 1990). Except insofar as any conventional carrier is incompatible with the active ingredient (e.g., hyperpolarized $^{89}Y$), its use in the therapeutic or pharmaceutical compositions is contemplated. The candidate substance (e.g., hyperpolarized $^{89}Y$) may comprise different types of carriers depending on its administration route and whether it needs to be sterile for such routes of administration, such as injection.

Administration to a subject of a composition comprising hyperpolarized $^{89}Y$ may take place via any method known to those of skill in the art. Due to the need for rapid detection once hyperpolarized $^{89}Y$ is prepared, a skilled artisan will understand the benefits of methods of administration that will work best with this detection limitation. One method of administration includes injection, such as intravenous injection, or injection into a muscle, eye, or tumor.

Sterile injectable solutions may be prepared, for example, by incorporating an active compound in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In particular embodiments, the composition is administered to a subject using a drug delivery device. Any drug delivery device is contemplated for use in delivering a pharmaceutically effective amount of a compound of the present invention.

The actual dosage amount of a composition of the present invention administered to a subject can be determined by physical and physiological factors such as body weight, severity of condition, the type of disease being imaged or treated, previous or concurrent therapeutic interventions, idiopathy of the subject and on the route of administration. The practitioner responsible for administration will, in any event, determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. More than one dose may be appropriate if a first dose is administered but an MRI image is not captured quickly enough. Multiple doses may be administered to, for example, provide the opportunity to obtain multiple scans of an area of a subject during one office visit.

In certain embodiments, pharmaceutical compositions may comprise, for example, at least about 0.1% of a compound of the present invention (e.g., a hyperpolarized $^{89}Y$-containing agent). In other embodiments, a compound of the present invention may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg/body weight, about 5 milligram/kg body weight, about 10 milligram/kg/body weight, about 20 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above.

A composition, such as a composition comprising $^{89}Y$ prior to hyperpolarization, must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

F. $^{89}Y$ and Imaging Techniques

Figure 4:
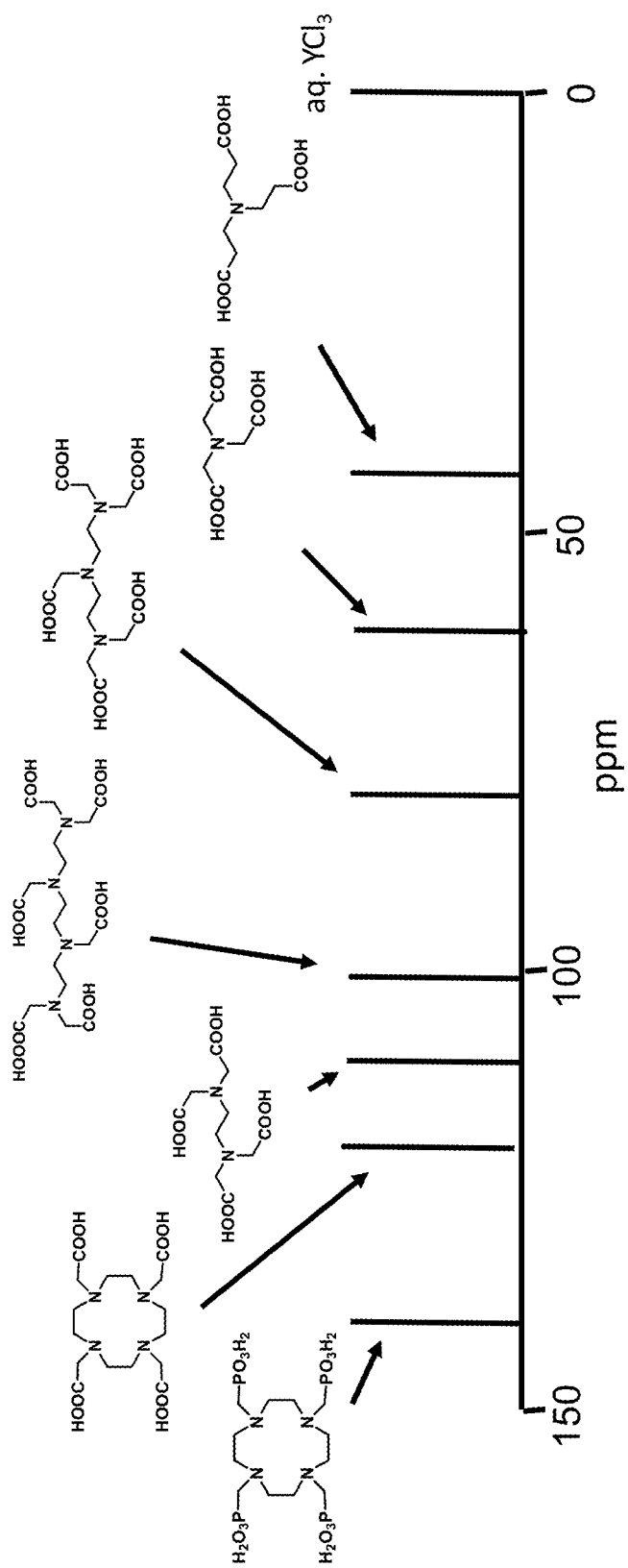
FIG. 4: The chemical shift values of the yttrium complex of various ligands ranges over 100 ppm. Relatively small changes in the ligand structure result in large shifts of the chemical shift value.

The current focus of many imaging techniques involves the design of sensors to specifically measure certain physiological parameters such as pH, temperature or to signal the presence of metabolites and biomarkers in tissues. Among the common spin ½ NMR active nuclei, $^{89}Y$ in its diamagnetic 3+ oxidation state has the longest $T_1$ relaxation time (600 s and perhaps even longer). This very long $T_1$ combined with its favorable spin quantum number (½), sharp NMR linewidth (3-5 Hz) and 100% natural abundance makes hyperpolarized $^{89}Y$ attractive as a potential in vivo imaging and spectroscopy probe. The extreme sensitivity of the chemical shift of $^{89}Y$ (III) to its chemical environment (FIG. 1) can be exploited in the design of sensitive probes to image and map physiological parameters such as pH, temperature, redox state, and glucose level in vivo. See FIG. 4.

1. pH Sensitive pH plays a key role in biological homeostasis, with small changes serving as indicators of various abnormalities. For example, healthy tissues have an extracellular pH around 7.4 while cancerous tissues are more acidic, typically having an extracellular pH of 6.8-6.9. Hyperpolarized yttrium complexes in which the coordination environment changes with pH are expected to show pH sensitive $^{89}Y$ chemical shifts. Examples of ligands that could be used to construct pH sensitive yttrium complexes are shown:

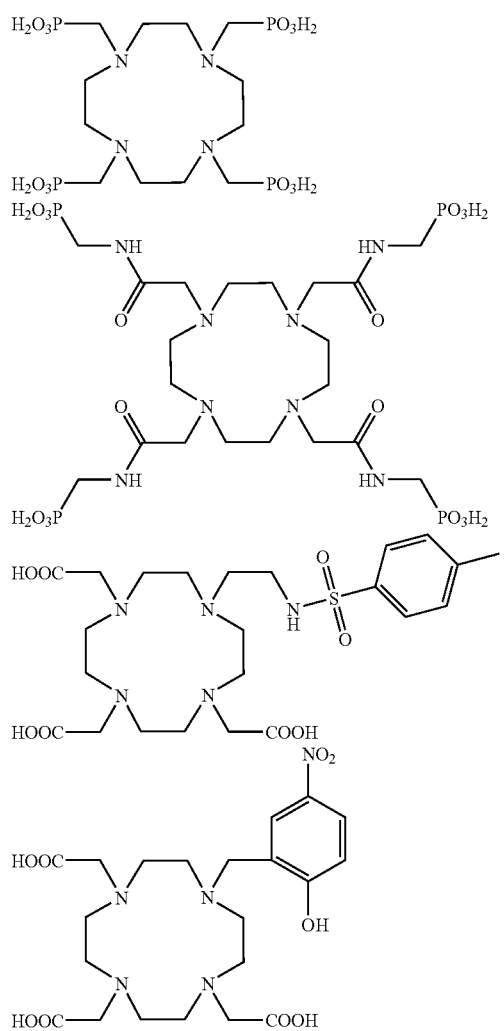

Woods et al. (2004); Zhang et al. (1999); Kalman et al. (2007).

2. Temperature Sensitive

The body temperature is tightly regulated and elevated temperatures in cancer as well as in some heart conditions have been demonstrated. A number of MRI techniques have been proposed to non-invasively image tissue temperature. The most widely used method is based on the measurement of proton resonance frequency shifts since the frequency of water proton resonance has a linear relationship with temperature over the range of 37-43° C. However, the accuracy of this method is only ±1-3° C., which limits its applicability. Since the $^{89}$Y chemical shift range is significantly larger than that of 1H chemical shifts, hyperpolarized yttrium complexes whose yttrium chemical shift shows temperature dependence could be used to measure and map temperature in vivo (Zhang et al., 2005; Hindman, 1996).

3. Glucose Sensors

D-glucose is an important energy source and metabolic intermediate for living cells. Glucose sensors based on electrochemical, ultraviolet, fluorescence or circular dichroism methods are invasive and not feasible for in vivo detection and mapping of glucose. Noninvasive detection of glucose by 1H magnetic resonance spectroscopy (MRS) is complicated by multiple overlapping metabolite signals with similar chemical shifts. Hyperpolarzied yttrium complexes in which the coordination environment of the Y3+-ion changes upon binding of could potentially. For example, ligands containing boronate groups can bind reversibly with sugar cis-diol groups changing the coordination environment around the yttrium (Zhang et al., 2003; Ren et al., 2008).

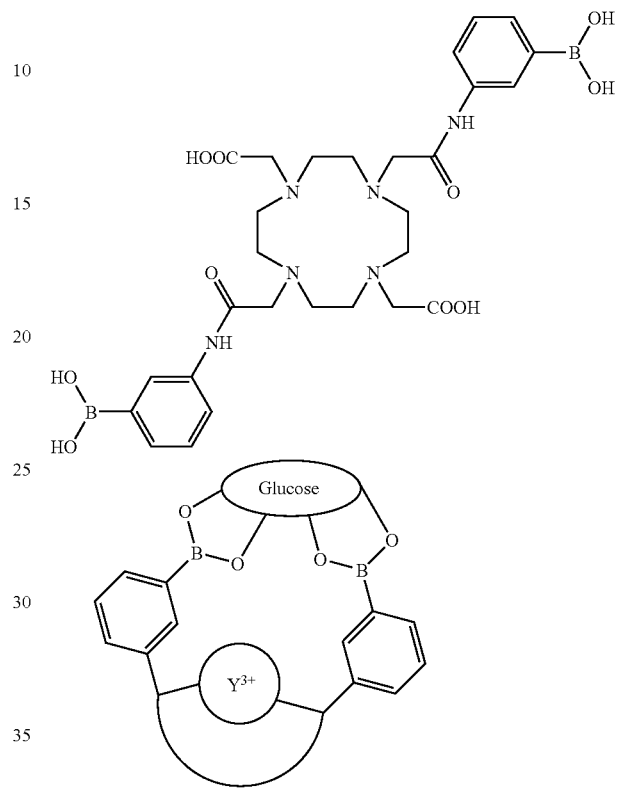

3. Lactate

L-Lactate, the end-product of anaerobic glycolysis, is known to be elevated in stroke, cancer, cysts, during brain activation, and a few other metabolic disorders. Seven coordinate yttrium complexes that can bind L-lactate as a bidentate ligand could be used to detect lactate. The binding of L-lactate to the Y$^{3+}$ coordination sphere will change the coordination environment and thus the chemical shift of yttrium (Terreno et al., 2003). An example of such ligand is shown:

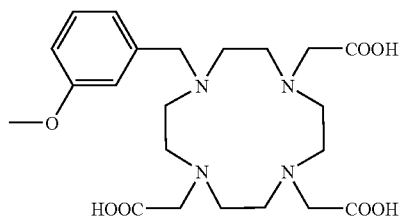 [SMILES: COc1cccc(CN2CCN(CC(=O)O)CCN(CC(=O)O)CCN(CC(=O)O)CC2)c1]

4. Zinc (II)

Zinc (II) is the second most abundant transition metal ion in mammalian tissues after iron. Zn$^{2+}$ participates in several biological processes such as apoptosis, regulation of synaptic transmission and cell death. Several Gd$^{3+}$ and Eu$^{3+}$ based Zn$^{2+}$ sensors with dipyridyl amine moieties that show strong affinity for zinc ions have been reported. These and similar ligands could also be used with hyperpolarized yttrium to detect Zn(II) as the coordination of Zn(II) by the dipyridyl moieties will alter the coordination environment of yttrium. An example of such ligands is shown:

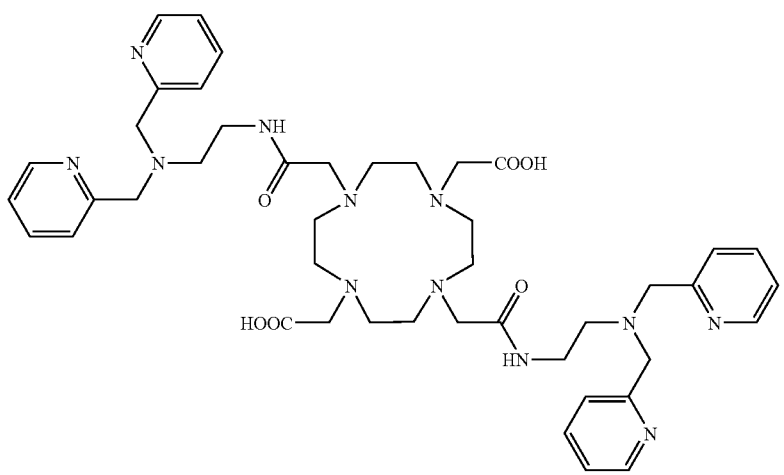 [SMILES: O=C(O)CN1CCN(CC(=O)NCCN(Cc2ccccn2)Cc2ccccn2)CCN(CC(=O)O)CCN(CC(=O)NCCN(Cc2ccccn2)Cc2ccccn2)CC1]

Esqueda et al. (2009).

5. Redox Sensor

Redox active species are tightly regulated in vivo under most circumstances. Overproduction of reactive oxygen species (ROS) is suspected to play a key role in Alzheimer's disease, Parkinson's disease, cancer, stroke, and atherosclerosis (Hoye et al., 2008). Therefore, the development of noninvasive imaging techniques to monitor tissue redox state is the focus of current research. Hyperpolarzied yttrium complexes containing a redox activatable moiety could be used to study tissue redox state. Several nicotinamide, quinoline, and acridine derivatives have been reported that are capable of mimicking the function of NAD/NADH redox system. Reversible oxidation/reduction of a nicotinamide analog moiety attached to the yttrium chelate will alter the coordination environment of yttrium as shown:

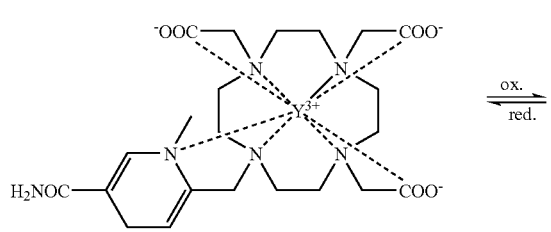

6. Enzyme-Activated Agents

The general design of enzyme activated hyperpolarized Y-complexes involves the linking of an enzyme substrate to a complex. Enzymatic catalysis alters the structure of the chelator molecule, thereby changing the coordination environment around the yttrium ion. An example is a ligand with a beta-galactopyranose group that can be cleaved with the enzyme beta-galactosidase. Removal of galactose moiety results in a change of the coordination environment (Moats et al., 1997).

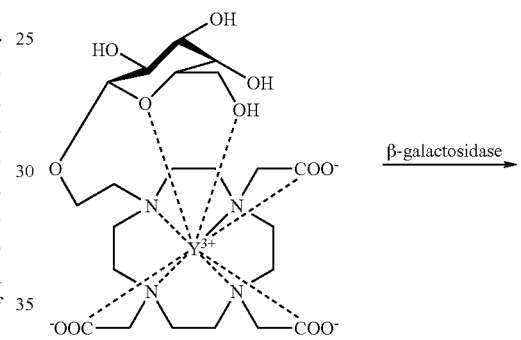

-continued

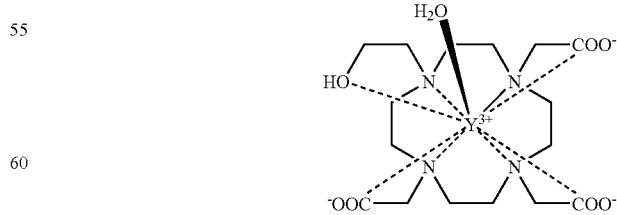

Enzyme activated ligands may contain other substrates such as peptides. For example, the Asp-Glu-Val-Asp (DEVD), sequence is cleaved by caspase-3, an "executioner" of the metabolic death cascade during cell apoptosis (Yoo et al., 2006).

G. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Dynamic Nuclear Polarization of $^{89}$Y-Containing Samples

Preparation of $^{89}$Y Complexes

Equivalent amounts of freshly prepared Y(OH)$_3$ was added to DTPA (Aldrich), DOTA (Macrocyclics) or DOTP (Macrocyclics) in water and the pH of the reaction mixture was brought to 5 by the addition of NaOH solution (2M). The reaction mixtures were stirred at 40° C. for 24 hours and the final pH was adjusted to 6 for Y(DTPA)$^{2-}$ and Y(DOTA)$^-$ and to 9 for Y(DOTP)$^{5-}$. The solutions were filtered and freeze-dried to give quantitative yields of the salt free complexes.

Hyperpolarization Studies 16.6 mM (Tris{8-carboxyl-2,2,6,6-tetra[2-(1-hydroxyethyl)]-benzo(1,2-d:4,5-d')bis(1,3)dithiole-4-yl}methyl sodium salt) radical in equal parts water/glycerol was used as a glassing matrix for the samples. To each sample was added a volume of glassing matrix equal to the initial sample volume. The sample was then placed in a hyperpolarizer (HyperSense, Oxford Molecular Biotools). 20 µL of YCl$_3$ (3.0 M) (Aldrich, (YCl$_3$.6H$_2$O)) and Y(DTPA)$^{2-}$ (1.52 M) or 40 µL of Y(DOTA)$^-$ (0.788 M), Y(DOTP)$^{5-}$ (1.0 M), and Y(DOTP)$_{5-}$ (0.5 M) were each polarized for 75±5 min. with a microwave irradiation of 100 mW at 94.118 GHz. The temperature was held at 1.4K during the polarization process. The samples were each then removed by injection of 4 mL of a solution of 850 µM EDTA in H$_2$O. 1.5 mL of the solution was subsequently transferred to an 8 mm NMR tube. This volume filled the detection coil only, thereby removing effects of diffusion that artificially increase the apparent Ti of the sample.

Spectrometer $^{89}$Y NMR spectra were recorded using a Varian 600 MHz NMR system in a 10 mm broad band probe tuned to 29.4 MHz. A single scan with a flip angle of 10 degrees (5.5 µs) was taken every 11 seconds (interpulse delay=10 s, acquisition time=1 s) starting approximately 30±1 seconds after ejection from the HyperSense device. Data collection continued until the signal was no longer distinguishable from the noise. The total number of 1 scan acquisitions for each sample was: YCl$_3$—100 scans, Y(DTPA)$^{2-}$—90 scans, Y(DOTA)$^-$—117 scans, and both Y(DOTP)$^{5-}$ samples—38 scans. The samples were each followed by collecting a thermal signal from 1.5 mL of YCl$_3$ (3 M) using a flip angle of 90 degrees (49.5 µs) and a single scan with the same receiver gain settings.

Polarization enhancements were calculated by comparing the integrated areas of the signal from the first acquisition from the hyperpolarized samples and that from the YCl$_3$ standard in Matlab (MathWorks, USA), taking into account the final concentrations and the difference in flip angles.

Patyal et al., 1997, had previously outlined a different method by which the polarization enhancement and the $T_1$'s of hyperpolarized samples could be measured. Due to the low sensitivity for their thermally polarized gas samples, the pulse flip angle had to be calibrated on the fly with a hyperpolarized sample. In the examples described herein, the flip angle is calibrated with a standard. Therefore, the following expression can be fitted as a function of number of inspection pulses to estimate the $T_1$ of the hyperpolarized species.

$$M_y(n) = M_p \cos^{(n-1)}\theta \sin\theta \exp^{-(n-1)TR/T_1}$$

$M_y$ is the transverse magnetization following a pulse of angle $\theta$, $M_p$ is the hyperpolarized Z-magnetization, TR is the experimental repetition time, and $T_1$ is the longitudinal relaxation time. The (n−1) term in the equation is derived from the magnetization retained from the previous scan.

Discussion of Results

Figure 2:
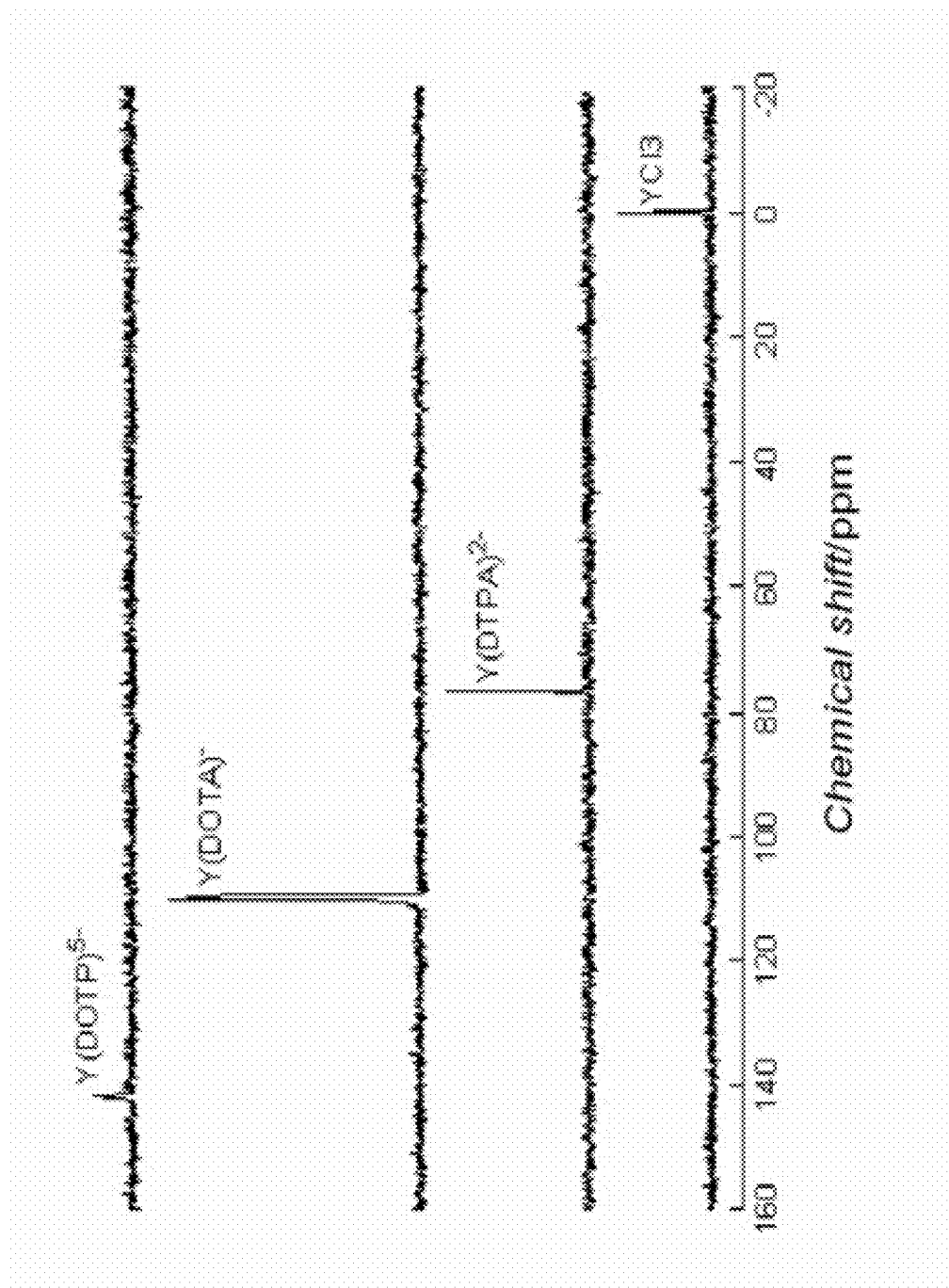
FIG. 2: NMR spectra of hyperpolarized $^{89}$Y complexes. Each spectrum was obtained on hyperpolarized sample ~30 seconds after transfer from the polarizer to a 8 mm NMR tube using a single 10° excitation pulse (see Table 1 for sample concentrations). The spectra were collected at 29.4 MHz using a 14.1 T magnet.

Dynamic nuclear polarization of frozen solutions consisting of YCl$_3$ or three different chelated forms of Y$^{3+}$ in the presence of a common stable trityl radical resulted in polarization enhancements that varied from 246 to 1527-fold above thermal equilibrium at 310K. This effort allowed for easy detection of the $^{89}$Y NMR signal using a single 10° pulse (FIG. 2). From an experimental standpoint, the necessity of reducing the sample volume by taking only a portion of the effluent from the dissolution process undoubtedly resulted in a loss of some magnetization due to $T_1$ processes before the NMR data collection ensued. In these efforts, the goal was to measure $T_1$ values on each sample by following the decay process so the sample volume was limited to 1.5 mL to ensure that the entire volume was sampled with each 10° pulse. If the volume of the sample is not restricted to the sample coil, diffusion will cause erroneous estimates of the $T_1$ due to the $\cos^{(n-1)}$ term in equation 1, above, making the $T_1$ appear artificially long. Other radicals may also produce desired polarizations. The polarization time may be varied from the 2.5 hours used here, as known in the art of hyperpolarization. In general, the DNP effect is mediated by the electron-nuclear dipolar interactions and the low gyromagnetic ratio of $^{89}$Y means that the polarization time constant is likely very long. Thus, higher polarization levels could be achieved by polarizing the samples longer.

The polarization enhancements reported in Table 1, below, were determined by comparison of the intensity of the polarized $^{89}$Y signal after the first 10° pulse to a 3M YCl$_3$ standard (single 90° pulse).

TABLE 1

Hyperpolarized $^{89}$Y data for YCl$_3$ and Y$^{III}$ complexes.

| Compound | Conc. in NMR tube (mM) | Measured enhancement | Measured $T_1$ (s) | Chemical shift (ppm) |
|---|---|---|---|---|
| YCl$_3$ | 15 | 246 | 620 | 0 (ref) |
| Y(DTPA)$^{2-}$ | 7.6 | 566 | 451 | 76 |
| Y(DOTA)$^-$ | 7.9 | 1527 | 499 | 109 |
| Y(DOTP)$^{5-}$ | 10 | 298 | 264 | 141 |
| Y(DOTP)$^{5-}$ | 5 | 1042 | 277 | 141 |

Comparison of the signal from hyperpolarized samples after full relaxation (thermal polarization) was impossible at these concentrations (mM). The polarization predicted for a sample cooled to 1.4K is 221 times greater than the Boltzmann thermal value at 310K. The measured enhancements of YCl$_3$ and Y(DOTP)$^{5-}$ were only slightly above this value so the effect due to DNP is only marginal in those cases. The remaining samples had polarizations well above that predicted for a cooled sample. It is interesting to note that the more highly charged species ($Y^{3+}$ and $Y(DOTP)^{5-}$) show the lowest polarization and, as the charge is reduced ($Y(DTPA)^{2-}$->$Y(DOTA)^-$), polarization increases. This may reflect less than optimal glass formation at 1.4K with the more highly charged species.

Figure 3:
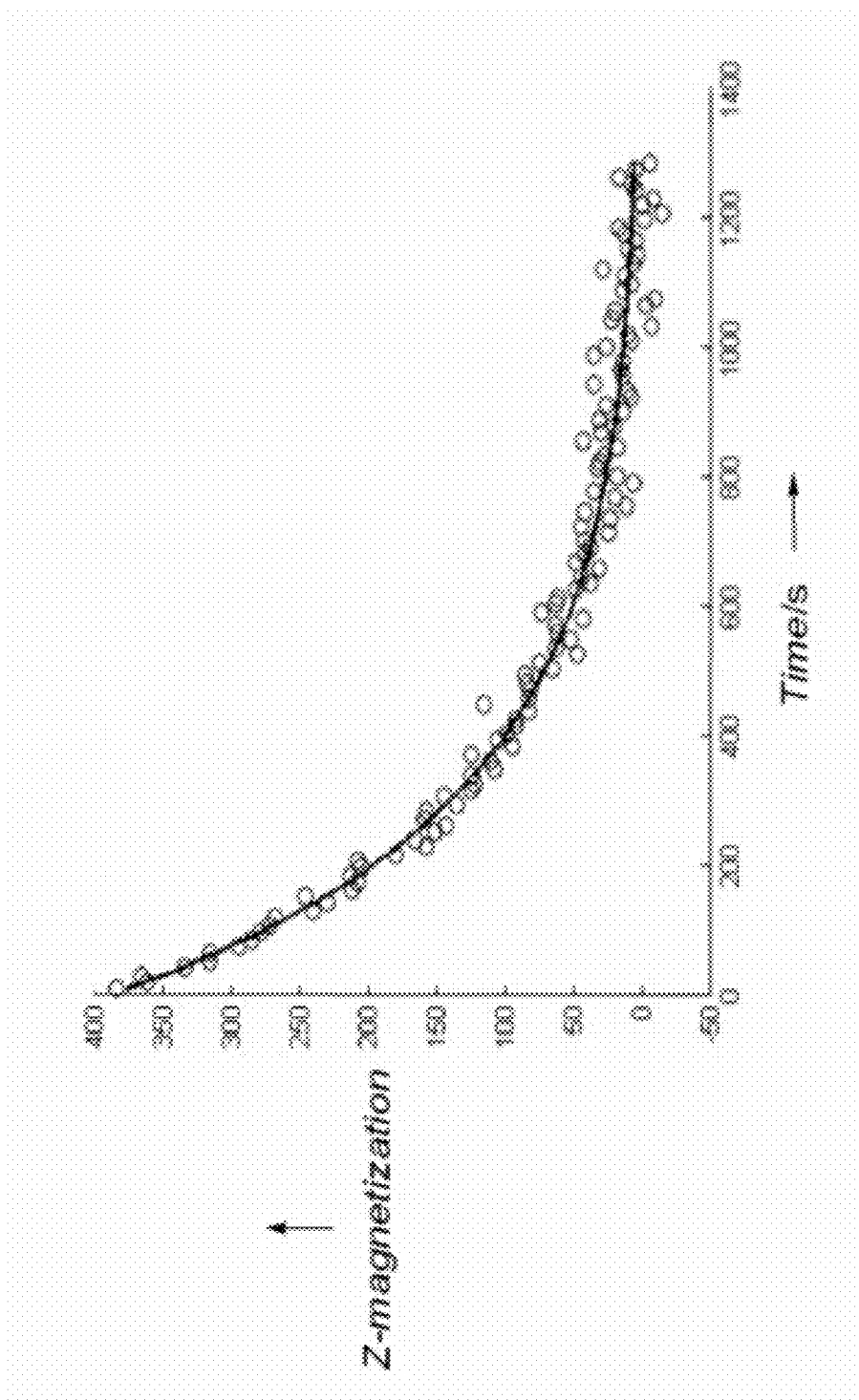
FIG. 3: NMR signal of $^{89}$Y(DOTA)$^-$ collected as a function of time after the sample was ejected from the polarizer, then inserted into the magnet. Total time following dissolution until the first acquisition was 30 seconds. The pH was 7 and final concentration of Y(DOTA)$^-$ in the NMR tube was 7.9 mM. The fitted line gave a $T_1$ of 499 seconds.

The $T_1$'s were measured by fitting the polarization decay curves (FIG. 3) to equation 1, above. The $T_1$ values reported previously for $Y(NO_3)_3$ on thermally polarized samples varied from 63-270 s depending upon concentration (1M samples gave longer $T_1$ values than 3M samples) (Levy et al., 1980). Estimates of $T_1$ obtained by following the decay of hyperpolarized $^{89}Y$ are even longer than those reported by Levy et al., 1980, by another factor of ~2.3 but the concentration of the hyperpolarized sample was also lower by a factor of ~67 so the trend reported by Levy et al. (1980) appears to hold over a very wide concentration range. It is unclear however whether this is simply an effect due to concentration or whether it partially reflects the experimental difficulty in measuring such long $T_1$ values for such an insensitive nucleus. In general, the $T_1$'s of the $^{89}Y$-chelates were found to be lower than that of the $YCl_3$ sample, also in contradiction to earlier results (Levy et al., 1980). One possible explanation for this observation is the higher $B_0$ field used here (14.1 Tesla) may have an additional chemical shift anisotropy contribution to the $T_1$ relaxation mechanism in the asymmetric environment of the chelates. It is also possible that other ligand spins in these samples ($^{14}N$, $^{31}P$) contribute to the relaxation of $^{89}Y$.

Example 2

Cross Polarization Method for Production of Hyperpolarized $^{89}Y$-Containing Samples Production of hyperpolarized (HP) $^{89}Y$ samples is handicapped by the long times (2.5 hours) needed for magnetization transfer between the free radical that is part of the sample matrix and the $^{89}Y$ nucleus. An alternative paradigm for producing HP $^{89}Y$ samples is to first transfer magnetization from the free radicals to the protons then use the cross polarization (CP) method to transfer polarization from the protons to the $^{89}Y$ nucleus. This can be accomplished by using any free radical: trityl, tempo, tempone, bdpa, etc. and any variant of the cross polarization technique, which uses applied alternating magnetic fields induced inside an NMR coil at matched frequencies to each nucleus simultaneously. This transfer can be performed at constant amplitude, with an increasing ramp of the amplitudes, or adiabatically. This change in methodology should allow samples to be produced on a 2 minute time scale.

Demonstration of the CP method has been shown for 5 samples of Y(DOTA) with a series of 5 different counter ions including tetra-butyl ammonium, potassium, tetramethyl ammonium, sodium, and ammonium. The spectra shown below appear from bottom to top in the order previously listed. See FIG. 5.

Preparation of the Complexes

The yttrium complexes were prepared by reacting zwitterionic DOTA (1,4,7,10-tetraazacyclododecane-1,4,7,10-tetraacetic acid) with freshly prepared yttrium hydroxide for 12 hours to give a clear solution. The pH was then adjusted to 6 by adding the appropriate base solution (tetra-butyl ammonium, potassium, tetramethyl ammonium, sodium, and ammonium hydroxide). The reaction mixtures were stirred for 24 hours, and the pH again was adjusted to 8. The solutions were filtered and freeze-dried to give the final complexes.

NMR

Cross polarization studies were carried out in a magnetic field of 14.1 Tesla with a Varian VNMRS NMR console using a Varian 3.2 mm T3 probe. Magic angle spinning was regulated at 5 kHz and the temperature was controlled at −50° C. Cross polarization was achieved at an applied $B_1$ field strength of 41.7 kHz at the $^{89}Y$ frequency. The proton B1 field strength was centered at 41.7 kHz and modulated by a tangent waveform to produce adiabatic transfer of polarization from the protons to the $^{89}Y$. CP times were set at either 12 or 16 ms. Proton decoupling was carried out at 80 kHz with an acquisition time of 15 ms. Interpulse delays for the CP studies were set according to the measured $T_1$ relaxation of the proton spin bath. Optimal CP times were obtained by arraying the CP time from 0 to 16 ms and picking the highest amplitude peak.

Results

The CP build up time constants, $T_{YH}$, were measured and are shown in Table 2. The normalized CP intensity (I) as a function of contact time (t), was fit according to the following (Smernik et al., 2002):

TABLE 2

Cross Polarization Build Up Time Constants and Proton $T_1$'s for Y(DOTA) Samples $$I = \left(1 - \frac{T_{YH}}{T_{1\rho}H}\right)^{-1}\left[1 - e^{\left(t\frac{1}{T_{1\rho}H} - \frac{1}{T_{YH}}\right)}\right]e^{\frac{-t}{T_{1\rho}H}}$$

| Sample | $T_{YH}$ (ms) | Proton $T_1$ (sec) |
|---|---|---|
| $Me_4N$ | 0.0072 | 1.3 |
| $NH_4$ | 0.0081 | 1.6 |
| K | 0.0058 | 4.7 |
| $Bu_4N$ | 0.0067 | 0.93 |
| Na | 0.004 | 4.7 |

The samples made with metal counter-ions ($Na^+$ and $K_+$) have slightly shorter build up time constants than the organic ions. Also, the $T_1$ of the protons in the complexes made with organic ions is considerably shorter. While this is important for repeating multiple scans, it should not have an impact on the DNP/CP technology, since the CP transfer should only need to be carried out once to transfer polarization from the hyperpolarized protons to the yttrium spins.

Discussion

The transfer of polarization from a hyperpolarized proton spin bath to $^{89}Y$ spins in the solid state is achievable even under the low RF field conditions characteristic of a probe built for a DNP pre-polarizer. The fact that many DNP pre-polarizers operate at 3.35 T provides an additional benefit in that $^{89}Y$ CSA becomes virtually negligible at these low field strengths. The efficiency of CP is optimal even in a DNP study where the sample must reside in a microwave cavity. The data further indicate that efficient CP is not restricted by choice of counter-ions, as the dipolar couplings of $^{89}Y$ spins to the distal protons are sufficient for polarization in all assayed conditions. (Gerfen et al., 1995).

Example 3

Hyperpolarized pH Responsive Agents

NMR and Hyperpolarzization Studies

Data was collected at a field strength of 9.4 T using a Varian VNMRS Direct Drive console. $^{89}Y$ NMR data was collected on an Oxford unshielded 89 mm widebore magnet, and $^{31}P$ NMR data was collected using a Varian premium shielded 54 mm narrow bore magnet. A 10 mm MR Resources low gamma probe was used to acquire $^{89}Y$ data and a Varian 5 mm AutoX Dual Broadband probe was used to acquire $^{31}P$ data.

Chemical shift assignments for $^{89}$Y spectra were referenced to a thermally polarized YCl$_3$ signal, and those for $^{31}$P were referenced to phosphoric acid. Free induction decays were acquired using a 90° hard pulse for all hyperpolarized $^{89}$Y and thermally polarized $^{31}$P studies.

For hyperpolarization studies, samples were polarized in an Oxford DNP Hypersense at 1.4K in a 3.35 T field, subject to 94.125 GHz of continuous microwave irradiation at 100 mW power. Samples containing 15 mM OX63 (tris{8-carboxyl-2,2,6,6-tetra[2-(1-hydroxyethyl)]-benzo(1,2-d:4,5-d') bis(1,3)dithiole-4-yl}methyl sodium salt) trityl radical and 140 to 180 mM of yttrium complex in a 75/25H$_2$O/glycercol glassing mixture were prepared. The samples were pre-frozen by pre-cooling the DNP cup in a bath of liquid nitrogen, and then pipetting the 160 μL of solution directly into the cup. Once the sample solution was frozen, it was placed into the cryostat of the hyperpolarizer for irradiation. During the final dissolution step, 4 mL of boiling water was injected to dissolve the sample.

Yttrium (III) complex of 1,4,7,10-tetraazacyclododecane-1,4,7,10-tetra(methylenephosphonic acid) (YDOTP)

1,4,7,10-tetraazacyclododecane-1,4,7,10-tetra(methylenephosphonic acid) (DOTP) was synthesized as reported in the literature (Lazar et al., 1992) The yttrium complex was prepared by reacting equimolar amounts of freshly prepared yttrium hydroxide and DOTP while maintaining the pH of the mixture at 9 for several days. The solution was filtered and the pH was adjusted to 7. The complex was obtained by freeze-drying the solution. The $^{89}$Y signal of the complex consisted of a quintet with an $^{89}$Y to $^{31}$P coupling constant of 6 Hz while the $^{31}$P NMR spectrum was a doublet showing the same coupling constant. These data are in agreement with the structure of YDOTP. See FIGs. B and C.

The pH Dependence of 89Y Chemical Shift of YDOTP

Figure 8:
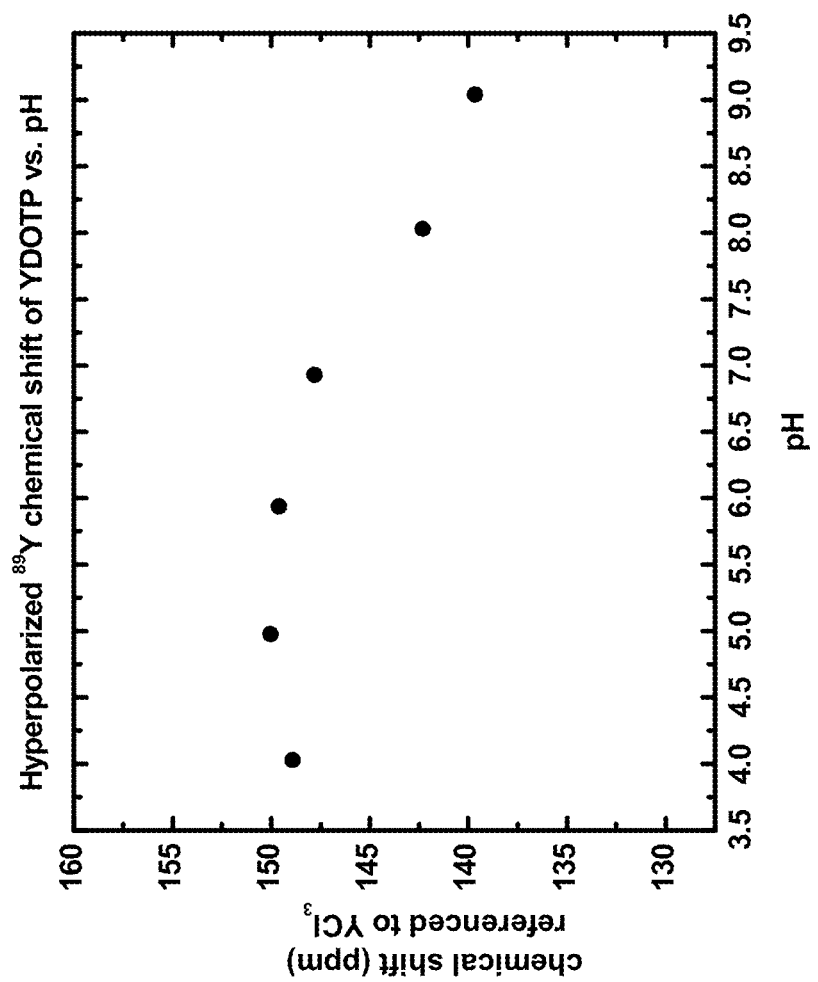
FIG. 8: The pH dependence of the $^{89}$Y chemical shift of YDOTP at 25 C.°.

Due to the relatively long T$_1$ of YDOTP, the entire hyperpolarized $^{89}$Y chemical shift versus pH data set was acquired from a single batch of hyperpolarized solution for this complex. Of the 4 mL of hyperpolarized YDOTP solution that was ejected from the Hypersense hyperpolarizer, 3.6 mL was divided evenly into six 10 mm NMR tubes, each of which contained a previously prepared 400 μL 1M buffer solution of pH 4, 5, 6, 7, 8, and 9 (acetate, acetate, MES, MOPS, TRIS, Bis-TRIS, respectively). This 1 mL sample solution was then thoroughly shaken to ensure proper mixing. Each tube was then placed in the magnet, one at a time, and a 90° hard pulse was administered. Upon completion of the experiment, the pH in each tube was measured and the results were within 1% of the original buffer value. The pH dependence of the $^{89}$Y chemical shift of YDOTP is shown in FIG. 8. The pH dependence of YDOTP is due to the protonation of the non-coordinating phosphonate oxygens, which occurs around pH 7.

Measurement Longitudinal Relaxation Time (T$_1$) Values of YDOTP

Figure 9:
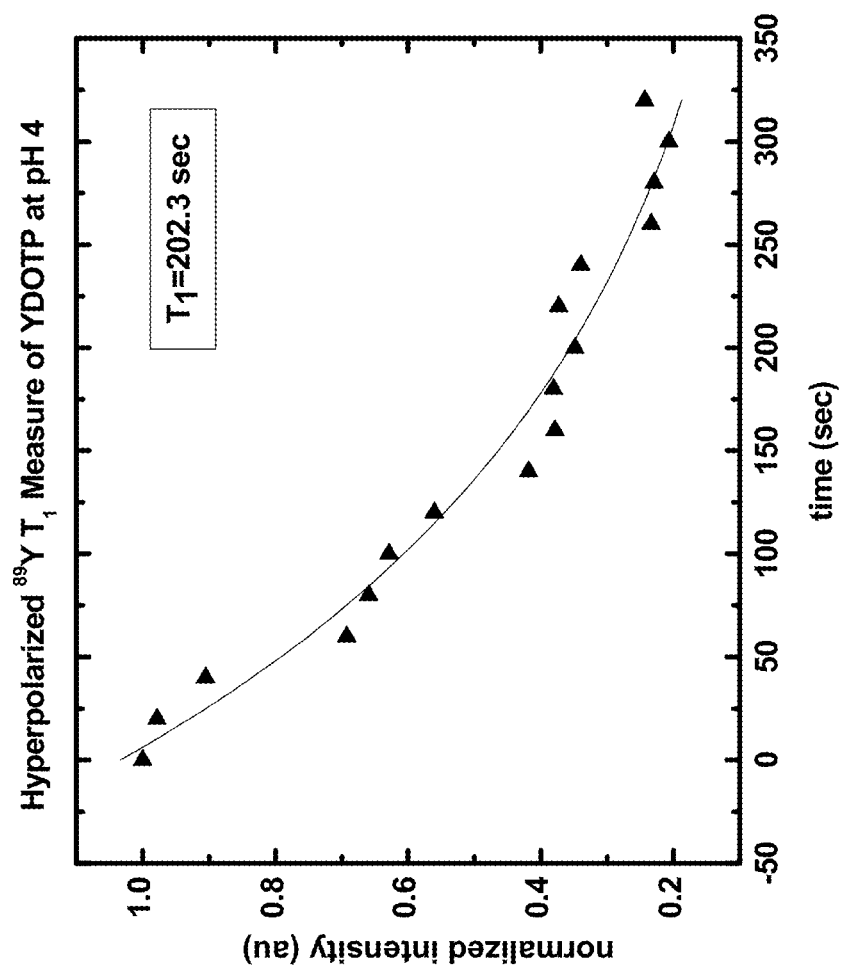
FIG. 9: The decay of the hyperpolarized 89Y signal of YDOTP at pH 4 at 25 C.°.

Longitudinal relaxation time (T$_1$) values of YDOTP were measured at pH 4 and 9 using hyperpolarized YDOTP. The measurements were performed using a 20° hard pulse and repetition time of 20 seconds. See FIG. 9.

Yttrium complex of 112-[[(p-toluenesulfonyl)amino] ethyl]-1,4,7,10-Tetraazacyclododecane-4,7,10-triacetic acid (YDO3ANTS)

The ligand 142-[[(p-toluenesulfonyl)amino]ethyl]-1,4,7, 10-tetraazacyclododecane-4,7,10-triacetic acid (DO3ANTS) was synthesized as described in the literature (Lowe et al., 2001). The yttrium complex was prepared by reacting equivalent amounts of DO3ANTS and freshly prepared yttrium hydroxide for several days while maintain the pH of the reaction mixture around 6. The pH was then raised to around 8.5 and the solution was filtered and the pH was adjusted to 7.5 and freeze-dried to give the final complex. 89Y NMR, H2O-D2O, pH 7.5, δ: 156 ppm (singlet).

The pH Dependence of $^{89}$Y Chemical Shift of YDO3ANTS

Figure 10:
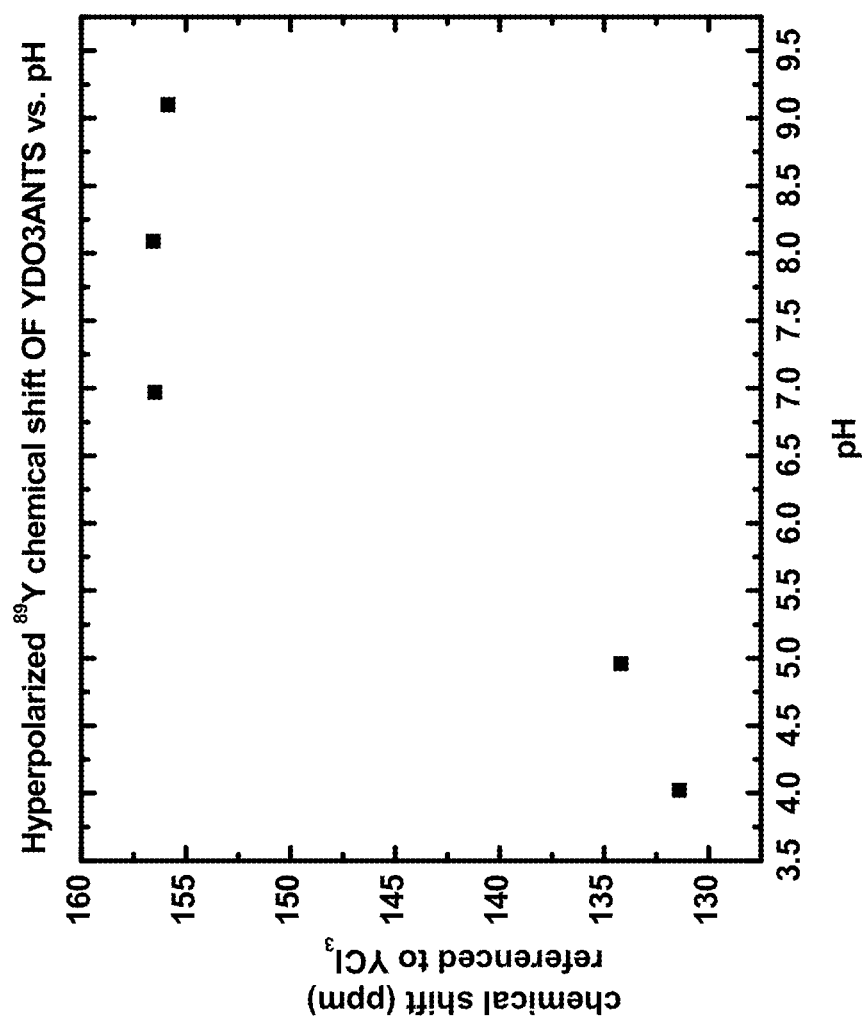
FIG. 10: The pH dependence of the $^{89}$Y chemical shift of YDO3ANTS at 25 C.°.

In contrast to YDOTP, hyperpolarized YDO3ANTS data was collected from multiple studies as the significantly shorter 89Y T$_1$ values of this complex precluded the collection of the $^{89}$Y chemical shift versus pH data set from a single batch of hyperpolarized solution. Of the 4 mL of hyperpolarized YDO3ANTS solution that was ejected from the hyperpolarizer, 3 mL was evenly divided into three 10 mm NMR tubes, each of which contained a previously prepared 500 μL 1M buffer solution of different pH—either 4, 5, 6, 7, 8, or 9 (acetate, acetate, MES, MOPS, TRIS, Bis-TRIS). This 1.5 mL mixture was then thoroughly shaken to ensure proper mixing. Each tube was then placed in the magnet, one at a time, and a 90° hard pulse was administered. Upon completion of the experiment, the pH in each tube was measured and the results were within 1% of the original buffer value. The pH dependence of the $^{89}$Y chemical shift of hyperpolarized YDO3ANTS is shown in FIG. 10. Interestingly, no $^{89}$Y signal was detected at pH 6, which is likely due to the intramolecular exchange process involving the pH dependent coordination of the beta-toluenesulfonamide nitrogen to the yttrium ion, which accounts for the pH dependence of the 89Y chemical shift.

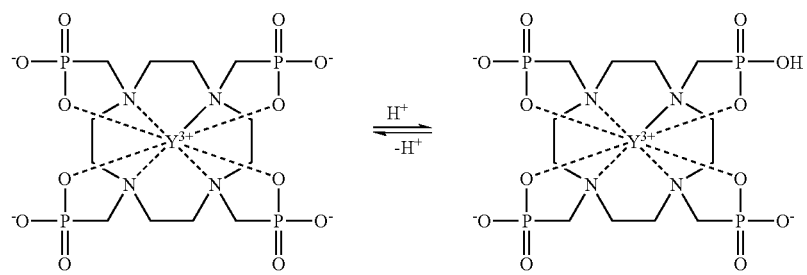

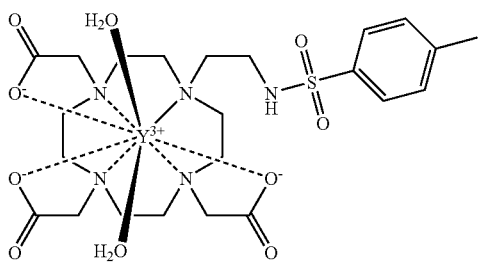 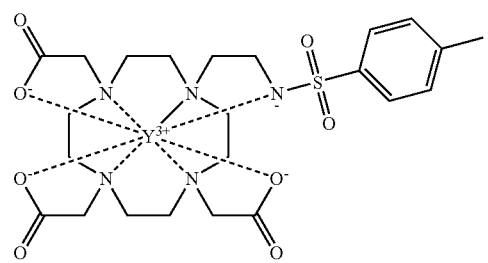

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Appln. 2006/0173282
Abragam and Goldman, In: *Nuclear Magnetism: Order and Disorder*, Oxford University Press, Oxford, 1982.
Adam et al., *J. Magn. Reson.*, 33:655, 1979.
Ardenkjaer-Larsen et al., *Proc. Natl. Acad. Sci. USA*, 100: 10158-10163, 2003.
Brun et al., *Phys. Rev.*, 76:1528, 1949.
Comment et al., *Concepts Magnetic Reson. (B) Magnetic Reson. Eng.*, 31B:255-269, 2007.
Day et al., *Nature Med.*, 13:1382-1387, 2007.
Esqueda et al., *J. Amer. Chem. Soc.*, 131(32):11387-11391, 2009.
Evans et al., *J. Amer. Chem. Soc.*, 112:4011-4030, 1990.
Gerfen et al., *J. Chem., Physics*, 102:9494, 1995.
Golman et al., *Proc. Natl. Acad. Sci. USA*, 103, 11270-11275, 2006a.
Golman and Petersson, *Acad. Radiol.*, 13:932-942, 2006b.
Golman et al., *Magnetic Reson. Med.*, 59:1005-1013, 2008.
Golman et al., *Proc. Natl. Acad. Sci. USA*, 100:10435-10439, 2003.
Hassler et al., *Phys.*, 280:117, 1977.
Hindman, *J. Chem. Phys.*, 44:4582, 1966.
Holz and Horrocks, *J. Magn Reson.*, 89:627-63, 1990.
Hoye et al., *Acc. Chem. Res.*, 41:87, 2008.
Hu et al., *J. Am. Chem. Soc.*, 126:10844-10845, 2004.
Kalman et al., *Inorganic Chem. (Washington, D.C.)*, 46(13): 5260-5270, 2007.
Kurhanewicz et al., *J. Nucl. Med.*, 49:341-344, 2008.
Lazar et al., *Inorganic Chem.*, 31(21):4422-4, 1992.
Levy et al., *J. Magnetic Reson.*, 40:167-173, 1980.
Lowe et al., *J. Amer. Chem. Soc.*, 123(31):7601-7609, 2001.
Maly et al., *J. Chem. Physics*, 128:N.PAG, 2008.
Merritt et al., *J. Amer. Chem. Soc.*, 129:12942-12943, 2007.
Merritt et al., *J. Magnetic Reson.*, 189:280-285, 2007b.
Merritt et al., *Proc. Natl. Acad. Sci. USA*, 104:19773-19777, 2007a.
Moats, *Angewandte Chemie, English Ed.*, 36(7):726-728, 1997.
Overhauser, *Physical Review*, 92:411-415, 1953.
Patyal et al., *J. Magnetic Reson.*, 126:58-651997, 1997.
PCT Appln. WO 91/12024
PCT Appln. WO 96/39367
PCT Appln. WO 97/09633
PCT Appln. WO 98/39277
Pu et al., *J. Org. Chem.*, 56:1280-1283, 1991.
Remington's Pharmaceutical Sciences, 18th Ed. Mack Printing Company, 1289-1329, 1990.
Ren et al., *Magn. Reson. Med.*, 60:1047, 2008.
Smernik et al., *Solid State NMR*, 22:71-82, 2002.
Terreno et al., *Inorganic Chem.*, 42(16):4891-4897, 2003.
Williams et al., *J. Amer. Chem. Soc.*, 113:9276-9286, 1991.
Williams, In: *Synthesis of Optically Active α-Amino Acids*, Pergamon Press, 1989.
Woods et al., *J. Amer. Chem. Soc.*, 126(30):9248-9256, 2004.
Yoo and Pagel, *J. Amer. Chem. Soc.*, 128:14032, 2006.
Zhang et al., *Angewandte Chemie, Intl. Ed.*, 38(21):3192-3194, 1999.
Zhang et al., *J. Amer. Chem. Soc.*, 125:15288, 2003.
Zhang et al., *J. Amer. Chem. Soc.*, 127:17572, 2005.

What is claimed is:

1. A hyperpolarized composition comprising a hyperpolarized $^{89}$Y-containing agent, a radical, a glassing agent and water.

2. The composition of claim 1, wherein the $^{89}$Y-containing agent comprises $^{89}$Y$^{3+}$.

3. The composition of claim 1, wherein the $^{89}$Y-containing agent is a salt or a complex that comprises $^{89}$Y$^{3+}$.

4. The composition of claim 1, wherein the $^{89}$Y-containing agent comprises a $^{89}$Y$^{3+}$ complex of an acyclic polyamine based ligand, a macrocyclic polyamine based ligand, a pyclen based ligand, a tripodal ligand, a cryptand, or a texaphyrin.

5. The composition of claim 4, wherein the $^{89}$Y-containing agent comprises a $^{89}$Y$^{3+}$-complex of an acyclic polyamine based ligand.

6. The composition of claim 5, wherein the acyclic polyamine based ligand is further defined as a compound of formula (I):

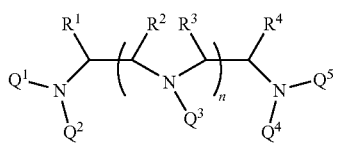

(I)

wherein:
$Q^1$-$Q^5$ are each independently hydrogen, $CHR^5COOR^6$, $CHR^5CONR^6R^7$, $CH_2CHR^5OH$, $CH_2CHR^5OR^6$, $CH_2CHR^5NR^6R^7$, $CHR^5P(O)R^6R^7$, or $CHR^5C(O)R^6$, wherein:
$R^1$-$R^7$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and
n=0, 1, or 2.

7. The composition of claim 6, wherein the compound of formula (I) is further defined as ethylenediaminetetraacetic acid (EDTA), diethylenetriaminepentaacetic acid (DTPA), nitrobenzyl-diethylenetriaminepentaacetic acid, diethylenetriaminepentaacetic acid bis(methylamide), or triethylenetetraminehexaacetic acid (TTHA).

8. The composition of claim 4, wherein the $^{89}Y$-containing agent comprises a $^{89}Y^{3+}$-complex of a macrocyclic polyamine based ligand.

9. The composition of claim 8, wherein the macrocyclic polyamine based ligand is further defined as a compound of formula (II):

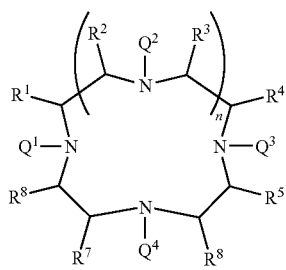

(II)

wherein:
$Q^1$-$Q^4$ are each independently hydrogen, $CHR^9COOR^{10}$, $CHR^9CONR^{10}R^{11}$, $CH_2CHR^9OH$, $CH_2CHR^9OR^{10}$, $CH_2CHR^9NR^{10}R^{11}$, $CHR^9P(O)R^{10}R^{11}$, or $CHR^9C(O)R^{10}$, wherein:
$R^1$-$R^{11}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and
n=0, 1, or 2.

10. The composition of claim 9, wherein the compound of formula (II) is further defined as 1,4,7,10-tetraazacyclododecane-1,4,7,10-tetraacetic acid (DOTA), 1,4,7,10-tetraazacyclododecane-1,4,7-triacetic acid (DO3A), 10-hydroxypropyl-1,4,7,10-tetraazacyclododecane-1,4,7-triacetic acid (HP-DO3A), 1,4,7,10-tetraazacyclododecane-1,4,7,10-tetraacetic acid (tetraglycine amide) (DOTAGly$_4$), p-nitrobenzyl-1,4,7,10-tetraazacyclododecane-1,4,7,10-tetraacetic acid (NO$_2$Bn-DOTA), 1,4,7,10-tetraazacyclododecane-1,4,7,10-tetramethylenephosphonic acid (DOTP), 1,4,7,10-tetraazacyclododecane-α,α',α'',α'''-tetramethyl-1,4,7,10-tetraacetic acid (DOTMA), 1,4,7,10-tetraazacyclododecane-1,7-diacetic acid-4,10-dimethylenephosphonic acid (DO2A2P), 1,4,7-triazacyclononane-1,4,7-triacetic acid (NOTA), or 7-[2-[bis(carboxymethyl)amino]ethyl]-1,4,7-triazacyclononane-1,4-diacetic acid (NETA).

11. The composition of claim 4, wherein the $^{89}Y$-containing agent comprises a $^{89}Y^{3+}$-complex of a pyclen based ligand.

12. The composition of claim 11, wherein the pyclen based ligand is further defined as a compound of formula (III):

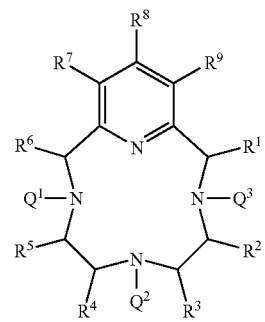

(III)

wherein:
$Q^1$-$Q^3$ are each independently $CHR^{10}COOR^{11}$, $CHR^{10}CONR^{11}R^{12}$, $CH_2CHR^{10}OH$, $CH_2CHR^{10}OR^{11}$, $CH_2CHR^{10}NR^{11}R^{12}$, $CHR^{10}P(O)R^{11}R^{12}$, or $CHR^{10}C(O)R^{11}$, wherein:
$R^1$-$R^{12}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond.

13. The composition of claim 12, wherein the compound of formula (III) is further defined as pyclen triacetic acid (PCTA, 3,6,9,15-tetraazabicyclo[9.3.1]pentadeca-1(15),11,13-triene-3,6,9-triacetic acid), p-nitrobenzylpyclen triacetic acid, cyclohexylpyclen triacetic acid, pyclen trimethylenephosphonic acid, or pyclen tri(methylenephosphonic acid monobutyl ester.

14. The composition of claim 4, wherein the $^{89}Y$-containing agent comprises a $^{89}Y^{3+}$-complex of a tripodal ligand.

15. The composition of claim 14, wherein the tripodal ligand is further defined as a compound of formula (IV):

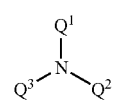

(IV)

wherein:
$Q^1$-$Q^3$ are each independently $CHR^1COOR^2$, $CHR^1CONR^2R^3$, $CH_2CHR^1OH$, $CH_2CHR^1OR^2$, $CH_2CHR^1NR^2R^3$, $CH_2CHR^1NCOR^4$, $CHR^1P(O)R^2R^3$, $CH_2CHR^1NCOR^4$, or $CHR^1C(O)R^2$, wherein:
$R^1$-$R^3$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; and
$R^4$ is alkyl, aryl, heteroaryl, hydroxypyridonyl, hydroxypyrimidinonyl, or hydroxyisoquinolinonyl.

16. The composition of claim 15, wherein the compound of formula (IV) is further defined as nitrilotriacteic acid, nitrilotris(methylenephosphonic acid), N,N',N"-(nitrilotri-2,1-ethanediyl)tris[1,2-dihydro-3-hydroxy-1-methyl-2-oxo-4-pyridinecarboxamide], N,N',N"-(nitrilotri-2,1-ethanediyl) tris[1,6-dihydro-1-hydroxy-6-oxo-2-pyridinecarboxamide], or N,N",N""-(nitrilotri-2,1-ethanediyl)tris[2,3-dihydroxy-N'-(2-hydroxyethyl)1,4-benzenedicarboxamide].

17. The composition of claim 1, wherein the $^{89}$Y-containing agent comprises a $^{89}$Y$^{3+}$-complex of a cryptand ligand.

18. The composition of claim 17, wherein the wherein the cryptand ligand is further defined as a compound of formula (V):

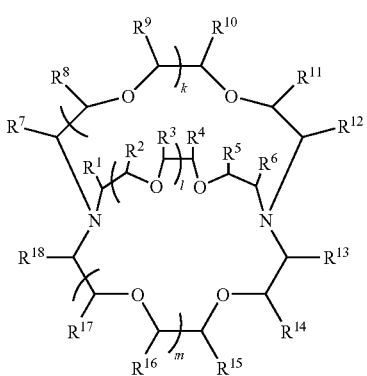

wherein:
$R^1$-$R^{18}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and
k, l and m are each independently =0, 1, or 2.

19. The composition of claim 18, wherein the compound of formula (V) is further defined as 4,7,13,16,21,24-hexaoxa-1,10-diazabicyclo[8.8.8]hexacosane (Cryptand[2.2.2]), 4,7,13,16,21-pentaoxa-1,10-diazabicyclo[8.8.5]tricosane (Cryptand[2.2.1]), dicyclohexylcryptand[2.2.2], dibenzocryptand[2.2.2], 4,7,13,16,21,24-hexaoxa-1,10-diazabicyclo[8.8.8]hexacosane-5-methanol, or 4,7,13,16,21-pentaoxa-1,10-diazabicyclo[8.8.5]tricosane-5-methanol.

20. The composition of claim 4, wherein the $^{89}$Y-containing agent comprises a $^{89}$Y$^{3+}$-complex of a texaphyrin ligand.

21. The composition of claim 20, wherein the texaphyrin ligand is further defined as a compound of formula (VI):

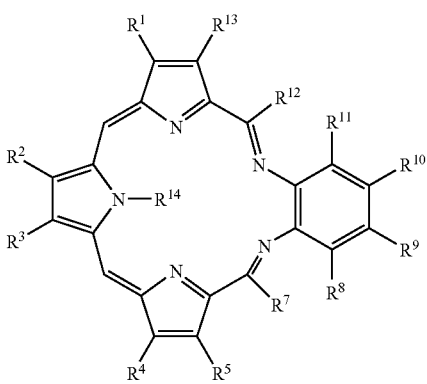

wherein:
$R^1$-$R^{13}$ are each independently hydrogen, hydroxyl, an amino acid or boronic acid containing group; or alkyl, aryl, heteroaryl, alkoxy, aryloxy, heteroaryloxy, aralkyl, acyl, or a substituted version of any of these groups; or may be taken with an adjacent R group to form an additional carbon-carbon bond; and
$R^{14}$ is hydrogen or lower alkyl, lower alkenyl, lower acyl or a substituted version of any of these groups.

22. The composition of claim 21, wherein the compound of formula (VI) is further defined as 9,10-diethyl-20,21-dimethoxy-4,15-dimethyl-8,11-imino-3,6:16,13-dinitrilo-1,18-benzodiaza-cycloeicosine-5,14-dipropanol, 9,10-diethyl-20,21-bis(3-hydroxypropoxy)-4,15-dimethyl-8,11-imino-3,6:16,13-dinitrilo-1,18-benzodiazacycloeicosine-5,14-dipropanol, or 9,10-diethyl-20,21-bis[2-[2-(2-methoxyethoxy)ethoxy]ethoxy]-4,15-dimethyl-8,11-imino-3,6:16,13-dinitrilo-1,18-benzodiazacycloeicosine-5,14-dipropanol.

23. The composition of claim 1, wherein the $^{89}$Y-containing agent is further defined as YCl$_3$, Y(DTPA)$^{2-}$, Y(DOTA)$^-$, or Y(DOTP)$^{5-}$.

24. The composition of claim 1, wherein the radical is a stable, water-soluble radical with an ESR linewidth between about 44 MHz and about 300 MHz at a magnetic field strength of 3.35 Tesla.

25. The composition of claim 1, wherein the radical is a trityl radical or a nitroxide radical.

26. The composition of claim 25, wherein the radical is a trityl radical.

27. The composition of claim 26, wherein the trityl radical is further defined as tris{8-carboxyl-2,2,6,6-tetra[2-(1-hydroxyethyl)]-benzo(1,2-d:4,5-d)bis(1,3)dithiole-4-yl}methyl sodium salt, OX63.

28. The composition of claim 25, wherein the radical is a nitroxide radical.

29. The composition of claim 28, wherein the nitroxide radical is TEMPONE, TEMPO, or TEMPOL.

30. The composition of claim 28, wherein the nitrogen of the nitroxide radical is further defined as $^{15}$N and the nitroxide radical comprises at least one deuterium atom.

31. The composition of claim 30, wherein the nitroxide radical is further defined as [$^{15}$N]-TEMPONE-d$_{16}$ or [$^{15}$N]-2,5-di(tert-butyl)-(3,4)-dimethoxycarbonyl pyrroloxyl-d$_2$.

32. The composition of claim 1, wherein the radical is further defined as a radical that comprises any of the following moieties: pentaarylcyclopentadienyl, bisphenylenediallyl (BDPA), galvinoxyl, or diphenylpicrylhydrazyl (DPPH).

33. The composition of claim 1, wherein the radical is further defined as chromium(V)-2-ethyl-2-hydroxybutanoate (Cr(V)-ehba).

34. The composition of claim 1, wherein the glassing agent is further defined as an alcohol having a molecular weight of about 250 g/mol or less.

35. The composition of claim 34, wherein the alcohol is further defined as glycerol, methanol, ethanol, or propanediol.

36. The composition of claim 1, wherein the glassing agent is further defined as dimethylsulfoxide.

37. The composition of claim 1, wherein the ratio of glassing agent to water ranges from about 10:90 to about 90:10.

38. The composition of claim 37, wherein the ratio of glassing agent to water ranges from about 40:60 to about 60:40.

39. The composition of claim 38, wherein the ratio of glassing agent to water is about 50:50.

40. The composition of claim 1, further defined as a liquid composition.

41. The composition of claim 1, further defined as a frozen composition.

42. A method of preparing hyperpolarized $^{89}$Y comprising hyperpolarizing a mixture of a $^{89}$Y-containing agent, a radical, a glassing agent and water.

43. The method of claim 42, wherein hyperpolarizing comprises subjecting the mixture to dynamic nuclear polarization.

44. The method of claim 42, wherein hyperpolarizing comprises subjecting the mixture to cross polarization.

45. The method of claim 42, further comprising freezing the mixture.

* * * * *

UNITED STATES PATENT AND TRADEMARK OFFICE
CERTIFICATE OF CORRECTION

PATENT NO.         : 8,697,034 B2                                               Page 1 of 1
APPLICATION NO.    : 12/576743
DATED              : April 15, 2014
INVENTOR(S)        : Zoltan Kovacs et al.

It is certified that error appears in the above-identified patent and that said Letters Patent is hereby corrected as shown below:

On the Title Page in item (57) ABSTRACT, line 2, insert two spaces between --$^{89}$Y.--
and --Hyperpolarized--.

In the Claims

In Claim 13 on column 34, line 40, delete "tetroazabicyclo" and insert --tetraazabicyclo-- therefor.

In Claim 18 on column 35, line 11, delete "wherein the".

Signed and Sealed this
Twenty-second Day of July, 2014

Michelle K. Lee
*Deputy Director of the United States Patent and Trademark Office*